(12) United States Patent
Clark et al.

(10) Patent No.: US 7,217,859 B2
(45) Date of Patent: May 15, 2007

(54) **GENETIC ELEMENTS FROM FBP3 OF *PETUNIA* CONFERRING FLOWER SPECIFIC TRANSGENE EXPRESSION**

(75) Inventors: David Grayson Clark, Gainesville, FL (US); Harry John Klee, Gainesville, FL (US); Kenichi Shibuya, Gainesville, FL (US); Holly Marie Loucas, Newberry, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 10/889,684

(22) Filed: Jul. 13, 2004

(65) Prior Publication Data
US 2005/0044586 A1    Feb. 24, 2005

Related U.S. Application Data

(60) Provisional application No. 60/487,969, filed on Jul. 17, 2003.

(51) Int. Cl.
*C12N 15/82* (2006.01)
*C07H 21/04* (2006.01)
*A01H 5/00* (2006.01)

(52) U.S. Cl. ................ 800/287; 800/278; 800/298; 435/419; 435/468; 435/320.1; 536/24.1; 536/23.6

(58) Field of Classification Search ........... 536/24.1, 536/23.6; 800/278, 287, 283; 435/320.1, 435/410, 419, 468
See application file for complete search history.

(56) References Cited

U.S. PATENT DOCUMENTS 5,424,200 A    6/1995  McPherson et al. ........ 435/70.1
6,388,173 B2 *  5/2002  Benfey et al. .............. 800/295

OTHER PUBLICATIONS

Vandenbussche M, Zethof J, Souer E, Koes R, Tornielli G, Pezzotti M, Ferroria S, Angenent GC, and Gerats T. (2003) Toward the Analysis of the Petunia MADS Box Gene Family by Reverse and Forward Transposon Insertion Mutagenesis Approaches: B, C, and D Floral Organ Identity Functions Require SEPALLATA-Like MADS Box Gene in *Petunia*. Plant Cell vol. 15, pp. 2680-2693.*
Vandenbussche MM, Zethof JL, and Gerats TG. (2003) GenBank Accession # AY370521.*
Maiti I.B. et al. Promoter/leader deletion analysis and plant expression vectors with the figwort mosaic virus (FMV) full length transcript (FLt) promoter containing single or double enhancer domains. (1997) Transgenic Research, vol. 6, pp. 143-156.*
Doelling J.H. et al. The minimal ribosomal RNA gene promoter of *Arabidopsis thaliana* includes a critical element at the trascription initiation site. (1995) Plant Journal, vol. 8, pp. 683-692.*
Chen S., et al. Minimal regions in the *Arabidopsis* PISTILLATA promoter responsive to the APETALA3/PISTILLATA feedback control do not contain a CArG box. (2000) Sex. Plant Reprod. vol. 13, pp. 85-94.*

Benfey P. N. et al. The Cauliflower Mosaic Virus 35S Promoter: Combinatorial Regulation of Transcription in Plants. (1990) Science, vol. 250, pp. 959-966.*
Kim Y. et al. A 20 nucleotide upstream element is essential for the nopaline synthase (nos) promoter activity. (1994) PMB, vol. 24, pp. 105-117.*
Bovy A. G. et al. Heterologous expression of the *Arabidopsis* etr1-1 allele inhibits the senescence of carnation flowers. (1999) Molecular Breeding, vol. 5, pp. 301-308.*
GenBank NP_176763, Feb. 19, 2004.
GenBank BAC43193, Feb. 14, 2004.
GenBank CAA50549, Feb. 10, 1994.
GenBank Q03488, Mar. 15, 2004.
Angenent, et al., "Petal and Stamen Formation in *Petunia* is Regulated by the Homeotic Gene fbp1", *The Plant Journal*, 4(1), 101-112, 1993.
Angenent, et al., "Co-suppression of the *petunia* homeotic gene fbp2 affects the identity of the generative meristem", *the Plant Journal*, 5(1), 33-44, 1994.
Chang, et al., "*Arabidopsis* Ethylene-Response Gene ETR1: Similarity of Product to Two-Component Regulators", *Science*, vol. 262, p. 539-544, 1993.
Angenent, et al., "Differential Expression of two MADS box genes in wild-type and mutant *petunia* flowers", *The Plant Cell*, vol. 4, p. 983-993, 1992.
Jorgensen, et al., "Chalcone synthase cosuppression phenotypes in *petunia* flowers: comparison of sense vs. antisense constructs and single-copy vs. complex T-DNA sequences", *Plant Molecular Biology*, 31:957-973, 1996.
Jefferson, "Assaying Chimeric Genes in Plants: The GUS Gene Fusion System", *Plant Molecular Biology Reporter*, vol. 5, No. 4, p. 387-405, 1987.
Wilkinson, et al., "A dominant mutant receptor from *Arabidopsis* confers ethylene insensitivity in heterologous plants", *Nature Biotechnology*, vol. 15, p. 444-447, 1997.
Knoester, et al., "Modulation of stress-inducible ethylene biosynthesis by sense and antisense gene expression in tobacco", *Plant Science*, 126, 173-183, 1997.

(Continued)

*Primary Examiner*—Ashwin D. Mehta
*Assistant Examiner*—Cathy Kingdon Worley
(74) *Attorney, Agent, or Firm*—McDonnell Boehnen Hulbert & Berghoff LLP

(57) ABSTRACT

The present invention provides recombinant promoters that drive tissue-specific expression, and transgenes comprising such recombinant promoters. Specifically, the invention provides transgenes comprising a recombinant promoter that drives tissue-specific expression of a heterologous nucleic acid molecule in a floral organ. The invention also provides methods for using such transgenes to produce a protein in a plant host cell or transgenic plant. The invention further provides methods for producing a transgenic plant that produces, for example, longer-lasting flowers, better fragrance, or better or longer-lasting color as compared to a wild type plant.

24 Claims, 5 Drawing Sheets

OTHER PUBLICATIONS

Jack, et al., "The Homeotic Gene APETALA3 of *Arabidopsis thaliana* encodes a MADS box and is expressed in petals and stamens", *Cell*, vol. 68, p. 683-697, 1992.

Knoester, et al., "Ethylene-insensitive tobacco lacks nonhost resistance against soil-borne fungi", *Proc. Natl. Acad. Sci.*, vol. 95, pp. 1933-1937, 1998.

Gubrium, et al., "Reproduction and Horticultural Performance of Transgenic Ethylene-insensitive *Petunias* ", *J. Amer. Soc. Hort. Sci.*, 125(3):277-281, 2000.

Clark, et al., "Root Formation in Ethylene-Insensitive Plants", *Plant Physiology*, vol. 121, p. 53-59, 1999.

Grotewold, et al., "The myb-Homologous P Gene Controls Phlobaphene Pigmentation in Maize Floral Organs by Directly Activating a Flavonoid Biosynthetic Gene Subset", *Cell*, vol. 76, p. 543-553, 1994.

Maiti, et al., "Promoter/leader deletion analysis and plant expression vectors with the figwort mosaic virus (FMV) full length transcript (FLt) promoter containing single or double enhancer domains", *Transgenic Research*, 6, 143-156, 1997.

Sessa, et al., "The Athb-1 and -2 HD-Zip domains homodimerize forming complexes of different DNA binding specificities", *The EMBO Journal*, vol. 12, No. 9, pp. 3507-3617, 1993.

Jefferson, et al., "GUS fusions: β-glucuronidase as a sensitive and versatile gene fusion marker in higher plants", *The EMBO Journal*, vol. 6, No. 13, pp. 3901-3907, 1987.

Lawton, et al., "Silencer region of a chalcone synthase promoter contains multiple binding sites for a factor, SBF-1, closely related to GT-1", *Plant Molecular Biology*, 16:235-249, 1991.

Fang, et al., "Multiple cis Regulatory Elements for Maximal Expression of the Cauliflower Mosaic Virus 35S Promoter in Transgenic Plants", *The Plant Cell*, vol. 1, 141-150, 1989.

Bovy, et al., "Heterologous expression of the *Arabidopsis* etr1-1 allele inhibits the senescence of carnation flowers", *Molecular Breeding*, 5:301-308, 1999.

Maiti, et al., "Isolation and Expression Analysis of Peanut Chlorotic Streak Caulimovirus (PCISV) Full-Length Transcript (FLt) Promoter in Transgenic Plants", *Biochemical and Biophysical Research Communications*, 244, 440-444, 1998.

Shibuya, et al., "The Centrol Rule of PhEIN2 in Ethylene Responses throughout Plant Development in Petunia", *Plant Physiology*, vol. 136, p. 2900-2912, 2004.

* cited by examiner

SEQUENCE LISTING

<160> NUMBER OF SEQ ID NOS: 16

<210> SEQ ID NO 1
<211> LENGTH: 1748
<212> TYPE: DNA
<213> ORGANISM: Arabidopsis thaliana

<400> SEQUENCE: 1

```
agaagatgga tgatttggca ttatgtgaag caaacaatgt tcctctaacc cccatgacgt      60
tcttgaagag agcttcagag tgttatccaa atcgaacttc aataatctac ggaaaaactc     120
gtttcacttg gcctcagacc tatgaccgtt gttgtcgtct agccgcttct ctaatctctc     180
ttaacatctc caagaacgat gtggtatcag ttatggctcc aaacacaccc gccttgtatg     240
aaatgcactt tgccgttccc atggctggag ctgtacttaa ccctatcaac actcgtctag     300
acgcaacatc cattgccgca atcctccgcc acgccaagcc caagatctta ttcctagacc     360
gcagttttga ggccttggct agagaaagcc tccatttatt atcatctgaa gactcaaacc     420
taaacttgcc ggtcatattt atccacgaga acgattttcc taaagggct tcattcgagg     480 agttagacta cgagtgtctc atccagaggg gagagcctac gccctcgatg gtggcacgca     540
```

-continued

```
tgttccgtat tcaagacgag catgatccaa tctccttaaa ctacacatcg ggtaccactg      600
ccgacccaaa aggtgttgtg attagccacc gaggagcata tttgtgcaca ttaagcgcga      660
ttattggttg ggaaatgggg acctgccctg tctacctttg gactctgcct atgtttcatt      720
gcaatggatg gacgtttaca tggggaaccg cggcgcgtgg gggtaccagt gtgtgtatga      780
ggcacgtgac tgccccggag atctataaaa acatagaaat gcataacgtg acacatatgt      840
gttgtgttcc tacggttttc aacattcttc tgaaaggaaa ttcacttgac ctgtcaccta      900
gatctggacc ggtccatgtg cttaccggag gttcaccgcc tcccgctgct cttgtcaaga      960
aagttcaacg gttgggggttt caagtgatgc atgcctatgg gcagaccgag gccactggtc     1020
caattttgtt ttgtgagtgg caagatgagt ggaatagatt accagagaat caacagatgg     1080
aattaaaagc caggcaaggg ataagcatct taggcctagc tgacgttgac gtgaaaaaca     1140
aggaaacgca aaagagtgct ccgcgcgatg aaagacaat gggagaaatc ctcattaaag      1200
gaagtagcat aatgaaaggg tatctaaaaa atcccaaagc tacatttgag gcatttaaac     1260
acggatggct caacacagga gatgtaggtg tgattcaccc tgatgggcac gtcgagatca     1320
aagatcggtc aaaagacata atcatatcgg gaggcgaaaa cattagtagt gttgaggtcg     1380
agaatgttct ttataagtac ccaaaagtcc ttgagactgc agttgtggcc atgcctcacc     1440
ctacgtgggg tgaaaccccg tgtgcgtttg ttgttctaga aaagagtgag actactatta     1500
aagaagatcg tgttgataaa tttcagacca gagagagaaa tctgattgag tattgccgtg     1560
aaaatctgcc acattttatg tgtccgagaa aagtggtgtt tttggaagaa ctgcccaaaa     1620
acgggaatgg aaagatcctt aagcctaagc taagagacat tgctaaaggt ttggttgttg     1680
aggatgagat caatgttata gctaaagaag ttaaacggcc ggttggacat tttatttcgc     1740
ggctttga                                                              1748
```

<210> SEQ ID NO 2
<211> LENGTH: 1164
<212> TYPE: DNA
<213> ORGANISM: Arabidopsis thaliana

<400> SEQUENCE: 2

```
catcgctgtc tggaagagct cggttcgagt catcgctgtc tggaacagcg atgactcgag       60
aaccgatctc ctccctctct ctcttaacca ctaagcaaaa atcccatctt tctatataaa      120
cctctctccc aactctgcta cttcccaccg taaatcgttt ctgggttctt aagaataaca      180
tggcctcgtc atcatcatca tcttatagat tccaatctgg gtcttaccct ctttcgtcaa      240
gtccttctct tgggaatttc gtcgaacgca ttaaagacgc ttgtcatttc cttgtctctg      300
ctgttttggc taccattatc tccgcgatct tgaccttctt cttcgcacta gtgggcacat      360
tgctagggc acttacagga gctttgatag gtcaagaaac tgagagtggt tcattagag       420
gagcagcaat tggagccatt cgggagctgt ttttctctat cgaggtcttt gaatcatctc      480
tggatctctg gaaatccgat gagtcgggtt tcggatgttt tctctacttg attgatgtca      540
ttgttagtct tctaagcggg agacttgtac gagagcgcat tggtcctgca atgctaagtg      600
cagtgcaaag tcaaatggga gctgtggata cagcttttga tgatcacaca agcctttttg      660
atacaggagg ctcaaaagga ttgacaggag accttgttga gaaatccca aagatgacaa       720
tcactggcaa caataacact gatgcttctg agaacacaga ctcatgttct gtttgtcttc      780
aggatttcca gctcggtgaa acagttagaa gcttgcctca ttgtcatcac atgtttcact      840
taccttgcat agacaattgg ctccttagac acggttcttg cccgatgtgt agacgtgata      900
```

```
tttaatctct tcatctctcc atcgtccgtc tctcataatg cagtttaacc tcgcagttca      960
gatatttcta cagctcgtac atcaagagtc tgctctgctc ttcttccctc ctccttgagt     1020
ttcatgtaaa ttccagttct tttggctgtt tacaattacg atacctctct tactctttca     1080
gagtcattgt aggactccta gttctctaat gtacaaagaa acacaaaaat agagtttttg     1140
ttttatctaa ttctttactc tggc                                            1164

<210> SEQ ID NO 3
<211> LENGTH: 904
<212> TYPE: DNA
<213> ORGANISM: Petunia x hybrida

<400> SEQUENCE: 3
ccactttcaa agccagtaac ttcaaagaga agtgagatat taggtatggg gagaggaaag       60
atagagataa agagaataga gaactctagc aacaggcaag ttacttactc caagagaaga      120
aatgggatta tcaagaaagc taaagaaatc actgttcttt gtgatgctaa ggtttcccttt    180 atcatctttg gtaattctgg caagatgcat gaatattgta gcccttctac tacgttacct     240
gatatgctgg atggttatca aaaaacttct gggaggaggc tatgggatgc taagcatgag     300
aacttgagca tgaaatcga  tagaatcaag aaagagaacg acagtatgca agttaagctc     360
aggcacctca aggagaaga  tatcaattct ttgaaccaca aagagcttat ggttttggaa     420
gaaggcttaa caaatggact ttctagtatc agtgccaagc agtcggagat cttgaggata     480
gtcaggaaaa atgatcaaat tctggaggag gaacacaagc aacttcaata tgctttgcac     540
caaaaggaga tggcagccat gggtggaaat atgagaatga ttgaagaagt gtaccatcaa     600
agagacaggg attacgaata ccagcagatg ccatttgccc ttcgagttca gccaatgcag     660
ccaaatctac atgaaagaat gtagagccta taattctact atatgcattt taaatgaaag     720
atcgttaaca atttagggta tgtactagaa gacttctaac tagtgatatg gtgaattaac     780
tagactattg cgggacaacc ttttcatgtg tgacaatata attatagtat attacctaat     840
ggttgtactg aatattgaag ttctcttcac ttcctacatg gttttaagta ttgatatgca     900
aaaa                                                                  904

<210> SEQ ID NO 4
<211> LENGTH: 780
<212> TYPE: DNA
<213> ORGANISM: Petunia x hybrida

<400> SEQUENCE: 4
ggaaaatatg gggagaggaa agatagagat aaaaagaata gaaaactcaa gcaacagaca       60
agtaacttac tcaaaaagaa gaaatgggat cttgaaaaaa gctaaggaaa ttagtgttct     120
ttgtgatgct cgtgtttctg ttatcatttt tgctagctct ggcaagatgc atgagttctc     180
ttctacttcg ttggttgata ttttggatca atatcacaag cttactggta gaagattgtt     240
ggatgctaag catgagaact tggacaatga atcaacaaa  gtcaagaaag acaatgacaa     300
catgcaaatt gaactcaggc acttgaaggg tgaagatatc acatctttga accatagaga     360
gctcatgata ttggaagatg cccttgaaaa tggactcact agtattcgta caaacagaa     420 tgaggttctg aggatgatga ggaaaaagac tcaaagtatg gaggaggagc aagaccaact     480
taattgccaa ttgcgccaac ttgagatagc aaccatgaat aggaatatgg gagaaattgg     540
cgaagtgttt cagcagaggg agaatcatga ctaccaaaac catatgcctt ttgccttccg     600
```

```
agtacaacca atgcagccaa atttgcagga gaggttgtaa aaaaagacct tgatctactt        660
ggtgacgacc ttttaatatt gtcttgtttg tattttgtgc tatcaaaaaa acttggtgtg        720
tattatcaag actcgtgtac cttatcgttt aagtgacatt atctatctat aagactaaaa        780

<210> SEQ ID NO 5
<211> LENGTH: 14
<212> TYPE: DNA
<213> ORGANISM: Phaseolus vulgaris

<400> SEQUENCE: 5
ctatggttaa atat                                                          14

<210> SEQ ID NO 6
<211> LENGTH: 14
<212> TYPE: DNA
<213> ORGANISM: Arabidopsis thaliana

<400> SEQUENCE: 6
ttaaaattat tgta                                                          14

<210> SEQ ID NO 7
<211> LENGTH: 14
<212> TYPE: DNA
<213> ORGANISM: Phaseolus vulgaris

<400> SEQUENCE: 7
taatagttaa taat                                                          14

<210> SEQ ID NO 8
<211> LENGTH: 14
<212> TYPE: DNA
<213> ORGANISM: Arabidopsis thaliana

<400> SEQUENCE: 8
atgaaattat tgtg                                                          14

<210> SEQ ID NO 9
<211> LENGTH: 2822
<212> TYPE: DNA
<213> ORGANISM: Petunia x hybrida cv Mitchell
<220> FEATURE:
<221> NAME/KEY: misc_feature
<222> LOCATION: (1411)..(1411)
<223> OTHER INFORMATION: n is a, c, g, or t

<400> SEQUENCE: 9
aagcttatta gctactcaac gatggttttt cctatttgaa tctcttccaa gagttcttgc        60
tctaataaag caactgaatc caatcaatac caaagctatg gttaaatatt ccaaacctta       120
agctaaaagg attaagaaat caacttaaga gtcaactccg ggcccacatg atcaaacccc       180
aaaattgagt ttactatcgc gttacctaca accatacgag ttataatata tattcaaaat       240
cttatcttgg tacgatttaa acctccaata gtcaattagt gttatagagt ttaagcctag       300
atttccaaaa ttcaaagatt caagcccaaa attagaatgt aaaaaacaca ccaaagacca       360
cagcctaaat aggaatagat atataactca acaaatccaa tgatttatat aatcactata       420
ttaagatata gtctaaaaat aataattata gcatgaacgc aagccaatta ccgatccctg       480
acattgaaat agagctaaga aaatgcacaa cagcttctca tttaagttca tcacactaag       540
caccctctat acctctaatg tgatagagct aaatgattag caaataattt atcccacttt       600
tcaatcattt gttatcatta ctttccatta ccatagtcac tattttttcat tatcaatgac       660
```

```
atcaaccatt tccatatcat aaatttatac agtaaccata ctaacctgga gcttgaacaa    720
ttatgaaggc ctccaaaggt ggatgtgcta ataccgtagc tcacagcttc ccctttttaag   780
atattttttgt ttttaacccct aaaagttaag acatggtctt atatatatag gccctagata  840
tattgagagg tagtagataa ataggcttag tctataaata accacttggc ccaaataaaa   900
tgtccatttg gtccaatagc ctattcatta ttctataatt ttattattat ctttaactca    960
atttaaatag aaaaaaata tttaatataa ataccggat tgttacaagt caactagaga     1020
gacagatgaa aagtggaaaa tgagttttct agaaagagaa agtgtgaaag aagaaagggt   1080
tgtcaaataa ttgtagaaaa atatttaaaa aataaaaata aaaatattt aaaagtgctc    1140
aaatttttaa gatcgcgaaa aaaggtgctc agcaaatcaa gaccatggtc agaagtgcac   1200
cattcacata aaaaatgatc tttttaatga gacaatcact aaaagttct ttttaatatg    1260
aggccagtga ggtgcttaat tagacccctt tctattatcc taatattatg tattttattt   1320
ataaactgaa ttgttagagg cagtacataa ttattcactt aattaattat gtctggagca   1380
cttcaaaact taaaataaga gaagaaaatg ncaaatgtcc tcattccaac aaagtgcttg    1440
ggagcttttg gctaagttca gtgtccatta ttctcaacca atagtaacta agaagtattg   1500
gtggaaggga atgcttcgga atggtaacca tcattttctt tgccactttc tccctctctt   1560
tcttattctg atattatgga tttaaaactc agtgttacca caactataaa gtcataatca   1620
gatgtagcta ttttgccgag gacactaatt agtttttttt atttatttat tgttttgcc    1680
tcataacaac ctaactcttt ggcctctata gctccacgaa tatatcagat ggtgatataa   1740
ggcagccaaa gttttttttt tgtggaaacc accatcagta agggtgctca tggttgatta   1800
tttgattcga tttttatgta aagcgaaaca aaccaaatta tttcggcgca tctacaggag   1860
tatatatacc aaatcaacca aatagtgtca atttttttttg gtttgatttt gtcgttttct   1920
tcaggtttcc agccttttctt ttgacgtttt aaaattacaa gttcatttca ttcaatcagt  1980
agagctaaca acgcagtttc gaatacgaac aaattgatta acttcttgtc tgctgataca   2040
tttatatgcg agaaattttg ccatgaaaca taacaattat tcacctttag aaatcaaata   2100
gcaacattac atccatatag gtttcgagct tacctagctt taatgacaag aataaagaaa   2160
cagcttttaa atagcgtcac tatagaagaa tagaaaactc aagcaagtac catgaatata   2220
tatgaaacat tttatggctg aaaaaatgtg tggtgtataa attatctata aagaataaaa   2280
tattatgatc ataaggattt ataaataaaa aaagtactt aattatgtag ctagttttaat   2340
tcaatatttt cttctaagta ccaaaccaaa tcaaatattg ccgattttt tcaaattta    2400
gatcaaacca aaccaagtca aaaaatatat tgaatattct tttatgtcag atttgatttg   2460
gttcgctttc ggttcttgtt gaactcccta gtaagtactg gtatttatca taataatcag   2520
ctgtcctcta tgatgtgtta aagcataggc agccgtatta gacattaaca tcaaattcca   2580
aaccatatcc acctaaacaa ccatttttgtg agcaatgttg gagatatggc tactctgcgc  2640
ttaataaacg ctgattcccc ccatatataa attacaatag ctgcacatct tcagcacaca   2700
ttttcccata taactcttcc tcattacaaa tttaagacca tatatcctac taaagaagtt   2760
cccccttccc catggacgag ttaccaaaat gtggagcaaa ctatgtgcct ctaactcctc   2820
ta                                                                  2822
```

<210> SEQ ID NO 10
<211> LENGTH: 2027
<212> TYPE: DNA

<210> SEQ ID NO 10
<211> LENGTH: 2027
<212> TYPE: DNA
<213> ORGANISM: Petunia x hybrida cv Mitchell

<400> SEQUENCE: 10

```
tgaagtgtgt gaagaaggaa catctcgacc ttgggctgca ggatcagtcc tcgtaactag      60
agggatttgc cctcgaagag agttgatcgc ctcatttatt cctctgttga cctccggctg     120
ttgctgcata aattcgaaga tcgtctcttg gaggttcctt taattagggg agagactcct     180
atggcgtcgt ctcctaggca gggttacgct cggagattgt ccatgcctgt gccgtggtct     240
tctgggtcct tgggaagaat attcttgccc gtcggatgag tagtctggag agtaattagg     300
gatgttctga ggggcacgtt cttgaccgtt gtccgccaca gtccgttgtg aatcgctttc     360
tgccatgtta gttcaaacaa aggatcgaca gaaagagta taatgcagga aaagacgaa       420
ctattaacct atagaggcta ttgaccggct cccactgtgg tcgctaaatt gtttaaccta     480
gatccaattt taggccaatt aacaattaaa tttgtatttg cggagtcacg atcaatagtt     540
tagattaaga gtttgcccaa attaaatacg gaattgcact aattaccaga ttatgatata     600
tatatatata tatatatata tatatatata tatatatata tatatatata tatatatata     660
tatatatata tatatatata tatatatata tatatatata tatatatata tatatatata     720
tatatatata tatatatata tatatatata tatatatata tatatatata tatatatata     780
tatatatata tatatatata tatatatata tatatatata tatatatatg cacgattacc     840
aatggagatg cgatggcaat aaatgatgat gtagaaataa tacgagatag ttaaagataa     900
ataagattaa agcgtgaata aaatagatag aaggaatcgt gtcggatcac ttgatcccgg     960
tgagaatttc ttgttactga ttatacttga aggcttgaga gaaaagtatc caacaaatgt    1020
aaacagagaa cggtattgag caagggtaaa gagagtattt tattggcacg attaccaatg    1080
gagatgcgat ggcaataaat gatgatgtag aaataatacg agatagttaa agataaataa    1140
gattaaagcg tgaataaaat agatagaagg aaccgtgtcg gatcacttga tcccggtgag    1200
aatttcttgt tactgattat acttgaaggc ttgagagaaa agtatccaac aaatgtaaac    1260
agaacggt attgagcaag agtaaagaga gtattttatt gatattgtag acagatgata    1320
gaatgtgtgt tacaatgatt cggaacgagt gctatttata gatctgctag gcatccgttg    1380
ggttttgtaac cactgggtat gtatccgttg gatacgtaac cgctgggtgt gtaactgttg    1440
ccttcatgac cattcattga gcaatcgcgt acgattaggt agccgctcat tcaaatcgca    1500
ttgatttggg aagcgttacg ttactgctct gggtctgctc gtagtaaccg tctagccagt    1560
cgcctgtctg ttagatgcct ctgcggagaa acctctgccc gtgccgcgtg gcagacacgt    1620
gtcacctttt tgagtgacgt cggttttttat ccaatacgag ttcaaattta taagtgcatg    1680
aattggctca ttgtcattgg ccatcatcca actaaaatgg atggatgttc atactcatca    1740
tcacttcaac agcggcacat gcatgagctt agcacgtgag tggtagctct aagctctaac    1800
tctcttaaat gctattttc tctgtatatt gtaccaccta taaatgcacc ccttttttctg    1860
ccataaactt ttaactacca tcacttgctc ttctttccaa tatcttagtc ctgaaattta    1920
actcccctaa ttctactttc tttattctct tttctatatc ttccagtgta tccaagtgcc    1980
tttgcagact tctggttaaa aaagctcatc tttcaatgat gaattac                  2027
```

<210> SEQ ID NO 11
<211> LENGTH: 3038
<212> TYPE: DNA
<213> ORGANISM: Petunia x hybrida cv Mitchell

<400> SEQUENCE: 11

```
gaatcgcaat tgtaaagaga aacaaataat taaggattaa tgagaaaaac aagaaagaaa      60
cgaaaagaaa aaaaaaagaa aaaaaaagta gtatagaaaa tagagtctttt cgttcattca     120 acataaccat atagtgctat ttctaataaa atatagggag aattacacaa atataccatc     180
ctaataccaa atttacaaaa aataccaata ctataccatt ttacaaaaca taccaatact     240 tttttttacaa atcatataca acttccatta aaaccataca aatgaaggtt ttaaaccctc     300
tcacacccac tgctcctagt cacagtgttg ccgccggtgg ccagccgccg ccgccggtg      360 gtggtagccg aaattttttta tttatttta tttttttttaa aaatctgaaa aaatatataa     420
aaaggtataa aaaacatcca aattacacat tcatacaaga tatacacttt tacaaaatag     480
aacgtacaaa atatacactt caatacatcc ccaaacatac aaagacataa aaataaattt     540
gtagatatgc aaaaaactta ttcatataca tatgaaatac acatacacat aaataccaaa     600
aatctacaaa aatatacaat atacaaaacc acaattttac caaacatacg cttgaaaata     660
taaaaataca caaatataca acaatataca aagatattca aaaaaaatta atgtattgat     720
gtaccaaaaa catacacata catataatac aaatcttata catgtttata caaataaaat     780
acacatacaa aaccaaaaaa agaaagaaag attgaggagc agatcggagc accagtgacg     840
gagcagtggc tcagccgccg tgagaataac agcagcgatg gggtggttgc cggcgagggg     900
gaggggacgg cggggtgggt ggataggggg aggagggaag agaaagagag agaaagagtg     960
ggaagaaatt agggtttttga gtttggggga gtgggaaatg aaaatggtat gttttgtaaa    1020
aatgtagaaa gtattgttat attgggtaaa atatttaaaa gtattggtat attatgtaat    1080
taagctatta agatagttat atagtgtaaa ttttcctaaa atatatatat gtccaatgag    1140
ctaactagaa acccataact ggtacctaat taagttgtaa agtcaaaaga tcatattatc    1200
cccttaatta aaatattgct ctaagtataa ttatataaaa gaaggtaaat acgtactcaa    1260
ataaataaaa aataaaagat tcaattataa aacatgcatc taaatggatt gagacaaaaa    1320
tttagagaat ataagagtt gcatttgata atctaattta gaataaattt atttgactaa    1380
tttaacagta caaatcgact tcatctacaa taaatacaaa ctactcatta gacatctgaa    1440
atgataaaaa attatctcaa ctgacggggg gaaaccaata aatcatcaaa tactttgttg    1500
aattttctat tcttctttta tttagtggac ttcaacatca tttcgaatat tctacctccc    1560
ataaattaaa attattgtaa attaggatta tatgttcaac tcttgtaaca cacaaattta    1620
ctttgcaaat gtcaactcta gtaagttcat tcctttttttt ttttttttaa tagaagcatt    1680
cctgaaacta tgtatttggt atgttattat tataaactag gataatatgt gcatgccctg    1740
ggatacacaa attaaagcag taaatgtgaa ctcgactagg tgcattctat ttttttaaca    1800
ctttctatga gcattcatga aataatatat gtattttttat gactaaggaa ttgtatttac    1860
tattttgttc gtcaaatagt aattatcttt gataatagtt gtattacaat ttcacgtgaa    1920
actaaaaata tatatgcaca aaaaaaaaaa ttatgttgtg attcactatt aagtatctct    1980
attcacaaaa actacaactt catttttatc agggtacat atcatgaaat tgataatgac    2040
ttcttaacca ttttaaggaa gatatatgtt gatcgaattt tggacaactt ctacataata    2100
ctatttttat tcgacaataa tttcttgata tgtgtgtgac cgtaaaaaag taggagtgtc    2160
ataaaaataa ggcagaaact ctagctaaca catgaagcat ttgaagctat agttgttgtt    2220
actcttattc acatttaaat tttgtgttat agaagtataa ataagtact atgatattaa    2280 cgaatgtcgt gttactcatc tttaaaattt aaaaatattt tcttactaat ataaattgca    2340
```

-continued

```
cgtgcaacgc acgtattaag aaactagtta actaataatt acaagtattc aaatgaaaat   2400
aaatgatgaa agcggataaa attttatgat actctcatag aaatgttgca cattttcttc   2460
gactcattac aacttaactc atcgtttgca ttttggtatt cctttttttt cttcagttcc   2520
ttttcgtcat taattttgga cgggaaaata ttaaataaat tctgaacttt tttgtttgtt   2580
tgagttcttt aacggtttaa catgcatgtt cgtccataat aatccactca ctactttcaa   2640
cttcaattct taacttaatc agtactttta tatttcaaac tttcaatcaa atattgttta   2700
gtccagaaaa aaaatcaaat tagttaggat aaaaaaaaaa gtgcaacaga tggctaagag   2760
cttttgtata atatttcatt aacaagctag taaagaaaga atcaaaggac aagatattaa   2820
cagtggtatg gctttgtcaa atgtccataa aaaacctact ttgctgagaa catagaaagt   2880
ttctggtctg ccaaacctct aatagaaata tgccattact ttcttcacat ctctttctat   2940
atcatcttct tcctcctctt agtactattc atcaaattaa attcccatat tctccacttt   3000
caaagccagt aacttcaaag agaagtgaga tattaggt                           3038
```

<210> SEQ ID NO 12
<211> LENGTH: 2247
<212> TYPE: DNA
<213> ORGANISM: Petunia x hybrida cv Mitchell

<400> SEQUENCE: 12

```
tttccacaca tccgatcttt cgggtcgtgc atatcgttct ctactaggag gcataggtgg     60
taattcagtt tcttcaggtt caccttgaaa ttgactagtg ggtgtttcat catctaaatt    120
agccccttcg gtattttctt catattgtgt ctctaacata tcattatcta gtggttgatc    180
aaaatttata tcatgcaaaa attgcgagtc atcttcctga gtaaaatcat ctagaagaga    240
aggagcgcta gaagtaccaa ctggtctttt acctaaagca ctatcatcct cccctcggtt    300
agaagcacgt gatctacgac cgctatccat aattgatctc cgcagttcag atatttttat    360
aattactaaa atatgcttca aacaaattac taaaatgtgc tacaaacaat aatattgcac    420
aaaaataaaa tagataataa aaagtaagaa cgagtttact tgatatcgtg aacttagaat    480
gtagattgta gaacttagga agtgaaagtt gaaacttgac cggaaccgca ccgaacaata    540
ttccacttca ctccaaatat ttttttgtaa tgcaatttag caaatagtct ttgtagaaat    600
aagagagatt gatagagatt tagagataat attagagaaa ttgtgaataa attgatgaaa    660
tacgatggta tttatagaaa aaaaaatagg ttggggggta tggggcgcct agggggggtgg    720
gggcaaaaaa tagccgtttt tggccgttgg gccaacggct gtgcgtgaaa tagccgttgg    780
ccaacatcta ttttttgcac aaagcccacc agattcgtcc ggtccggtcc agtccagacc    840
ggttccggtt cactttggtc cggttcatcc ggtccatttt ggaggtgacg gatcggaaac    900
gtgtcgtttt ttttttaata tttggccggg cttgcgccgg tccggtccgg tccggcccgg    960
tgcaaaccgg gctattagac agccttactt ctaacacaac tactcatcaa tttcaaataa   1020
attgggaagg actacattaa tccttactga tcatgtttct tcatttaaac tcaatttatg   1080
acttatgtca tcatcctacc aaataaataa caaaagtaaa aaattaataa gttaaatgtg   1140
tgtgtgtgtg tgtgtctata tatatatata tataaagaag taataataat gatacttcta   1200
ataataataa tatagaaata attatcgatt gtttaccagc ataactctgt ttgtgagctt   1260
acttacattg tcagtccaaa ctcgactaaa ggaggaggat tgcagtaggc tggcttgcca   1320
gcgtaaaatt ttaccaatca tgacgaatcc tcataataca gatattattt atcacatgta   1380
tagatatttt tcttccatct tatgatattt ttagctgaat ttgcattaat tctaggtatt   1440
```

-continued

```
tgtaggtctt caagctaatt tatgtccatg tgattttaag tctacattgt tcaattttaa    1500
catattttca ctagtttcat acctaggtca atgtcaaata tgactaaatc atcccaaccg    1560
atattccctt atttgagccc caacgtgtgc tacttgcacc ttctagaaaa tgtaatattc    1620
ccttcgttct acaaaagatg gcacaattcg gacttcaaga gtcacacgtt ttagttttgg    1680
ccgtaaactt ggacataaaa tcattaaatt tcttaatata aagtttatat attcggacac    1740
tatataaaaa gtaacatata taagtcataa tagttaataa tttaaaacat ctaacatgaa    1800
attattgtgg tgaaagaaag actcgactct tcaaattcga cttgtgtcat cttttgtaga    1860
aatgatggag taattctttta gtaccacaat tatccaccttt tatgttgaag tagaatgaga    1920
tctttaacac cagccggtta aaaaaatcac taatttaagc ttttagatta cacaattcaa    1980
ctagagagag atgagaagat ggagaaaaaa ccaaaggata agaaggtgaa agaaaagggt    2040
taagaggagg ggctttaatg cagatggagt tggctttgtc aaataccttaa aaacaaacca    2100 acttttttctg aaacttaaga aagttgattg tctgtcaatc cttaaataga tattcccatt    2160
aattcatttc ttctcctttt gcaactctat cattatatac ttgttcttct caagcaaaag    2220
aatagtccaa caagagaaag ggaaaat                                         2247
```

<210> SEQ ID NO 13
<211> LENGTH: 580
<212> TYPE: PRT
<213> ORGANISM: Arabidopsis thaliana

<400> SEQUENCE: 13

```
Met Asp Asp Leu Ala Leu Cys Glu Ala Asn Asn Val Pro Leu Thr Pro
1               5                   10                  15

Met Thr Phe Leu Lys Arg Ala Ser Glu Cys Tyr Pro Asn Arg Thr Ser
            20                  25                  30

Ile Ile Tyr Gly Lys Thr Arg Phe Thr Trp Pro Gln Thr Tyr Asp Arg
        35                  40                  45

Cys Cys Arg Leu Ala Ala Ser Leu Ile Ser Leu Asn Ile Ser Lys Asn
    50                  55                  60

Asp Val Ser Val Met Ala Pro Asn Thr Pro Ala Leu Tyr Glu Met
65                  70                  75                  80

His Phe Ala Val Pro Met Ala Gly Ala Val Leu Asn Pro Ile Asn Thr
                85                  90                  95

Arg Leu Asp Ala Thr Ser Ile Ala Ala Ile Leu Arg His Ala Lys Pro
            100                 105                 110

Lys Ile Leu Phe Leu Asp Arg Ser Phe Glu Ala Leu Ala Arg Glu Ser
        115                 120                 125

Leu His Leu Ser Ser Glu Asp Ser Asn Leu Asn Leu Pro Val Ile
    130                 135                 140

Phe Ile His Glu Asn Asp Phe Pro Lys Arg Ala Ser Phe Glu Glu Leu
145                 150                 155                 160

Asp Tyr Glu Cys Leu Ile Gln Arg Gly Glu Pro Thr Pro Ser Met Val
                165                 170                 175

Ala Arg Met Phe Arg Ile Gln Asp Glu His Asp Pro Ile Ser Leu Asn
            180                 185                 190

Tyr Thr Ser Gly Thr Thr Ala Asp Pro Lys Gly Val Val Ile Ser His
        195                 200                 205

Arg Gly Ala Tyr Leu Cys Thr Leu Ser Ala Ile Ile Gly Trp Glu Met
    210                 215                 220
```

```
Gly Thr Cys Pro Val Tyr Leu Trp Thr Leu Pro Met Phe His Cys Asn
225                 230                 235                 240

Gly Trp Thr Phe Thr Trp Gly Thr Ala Ala Arg Gly Thr Ser Val
            245                 250                 255

Cys Met Arg His Val Thr Ala Pro Glu Ile Tyr Lys Asn Ile Glu Met
            260                 265                 270

His Asn Val Thr His Met Cys Cys Val Pro Thr Val Phe Asn Ile Leu
            275                 280                 285

Leu Lys Gly Asn Ser Leu Asp Leu Ser Pro Arg Ser Gly Pro Val His
290                 295                 300

Val Leu Thr Gly Gly Ser Pro Pro Ala Ala Leu Val Lys Lys Val
305                 310                 315                 320

Gln Arg Leu Gly Phe Gln Val Met His Ala Tyr Gly Gln Thr Glu Ala
            325                 330                 335

Thr Gly Pro Ile Leu Phe Cys Glu Trp Gln Asp Glu Trp Asn Arg Leu
            340                 345                 350

Pro Glu Asn Gln Gln Met Glu Leu Lys Ala Arg Gln Gly Ile Ser Ile
            355                 360                 365

Leu Gly Leu Ala Asp Val Asp Val Lys Asn Lys Glu Thr Gln Lys Ser
370                 375                 380

Ala Pro Arg Asp Gly Lys Thr Met Gly Glu Ile Leu Ile Lys Gly Ser
385                 390                 395                 400

Ser Ile Met Lys Gly Tyr Leu Lys Asn Pro Lys Ala Thr Phe Glu Ala
            405                 410                 415

Phe Lys His Gly Trp Leu Asn Thr Gly Asp Val Gly Val Ile His Pro
            420                 425                 430

Asp Gly His Val Glu Ile Lys Asp Arg Ser Lys Asp Ile Ile Ser
            435                 440                 445

Gly Gly Glu Asn Ile Ser Ser Val Glu Val Glu Asn Val Leu Tyr Lys
450                 455                 460

Tyr Pro Lys Val Leu Glu Thr Ala Val Val Ala Met Pro His Pro Thr
465                 470                 475                 480

Trp Gly Glu Thr Pro Cys Ala Phe Val Val Leu Glu Lys Ser Glu Thr
            485                 490                 495

Thr Ile Lys Glu Asp Arg Val Asp Lys Phe Gln Thr Arg Glu Arg Asn
            500                 505                 510

Leu Ile Glu Tyr Cys Arg Glu Asn Leu Pro His Phe Met Cys Pro Arg
            515                 520                 525

Lys Val Val Phe Leu Glu Glu Leu Pro Lys Asn Gly Asn Gly Lys Ile
530                 535                 540

Leu Lys Pro Lys Leu Arg Asp Ile Ala Lys Gly Leu Val Val Glu Asp
545                 550                 555                 560

Glu Ile Asn Val Ile Ala Lys Glu Val Lys Arg Pro Val Gly His Phe
            565                 570                 575

Ile Ser Arg Leu
            580

<210> SEQ ID NO 14
<211> LENGTH: 241
<212> TYPE: PRT
<213> ORGANISM: Arabidopsis thaliana

<400> SEQUENCE: 14

Met Ala Ser Ser Ser Ser Ser Tyr Arg Phe Gln Ser Gly Ser Tyr
1               5                   10                  15
```

```
Pro Leu Ser Ser Pro Ser Leu Gly Asn Phe Val Glu Arg Ile Lys
            20                  25                  30

Asp Ala Cys His Phe Leu Val Ser Ala Val Leu Ala Thr Ile Ile Ser
        35                  40                  45

Ala Ile Leu Thr Phe Phe Ala Leu Val Gly Thr Leu Leu Gly Ala
    50                  55                  60

Leu Thr Gly Ala Leu Ile Gly Gln Glu Thr Glu Ser Gly Phe Ile Arg
65                  70                  75                  80

Gly Ala Ala Ile Gly Ala Ile Ser Gly Ala Val Phe Ser Ile Glu Val
                85                  90                  95

Phe Glu Ser Ser Leu Asp Leu Trp Lys Ser Asp Glu Ser Gly Phe Gly
            100                 105                 110

Cys Phe Leu Tyr Leu Ile Asp Val Ile Val Ser Leu Ser Gly Arg
            115                 120                 125

Leu Val Arg Glu Arg Ile Gly Pro Ala Met Leu Ser Ala Val Gln Ser
130                 135                 140

Gln Met Gly Ala Val Asp Thr Ala Phe Asp Asp His Thr Ser Leu Phe
145                 150                 155                 160

Asp Thr Gly Gly Ser Lys Gly Leu Thr Gly Asp Leu Val Glu Lys Ile
                165                 170                 175

Pro Lys Met Thr Ile Thr Gly Asn Asn Asn Thr Asp Ala Ser Glu Asn
            180                 185                 190

Thr Asp Ser Cys Ser Val Cys Leu Gln Asp Phe Gln Leu Gly Glu Thr
            195                 200                 205

Val Arg Ser Leu Pro His Cys His Met Phe His Leu Pro Cys Ile
    210                 215                 220

Asp Asn Trp Leu Leu Arg His Gly Ser Cys Pro Met Cys Arg Arg Asp
225                 230                 235                 240

Ile

<210> SEQ ID NO 15
<211> LENGTH: 212
<212> TYPE: PRT
<213> ORGANISM: Petunia x hybrida

<400> SEQUENCE: 15

Met Gly Arg Gly Lys Ile Glu Ile Lys Arg Ile Glu Asn Ser Ser Asn
1               5                   10                  15

Arg Gln Val Thr Tyr Ser Lys Arg Arg Asn Gly Ile Ile Lys Lys Ala
            20                  25                  30

Lys Glu Ile Thr Val Leu Cys Asp Ala Lys Val Ser Leu Ile Ile Phe
        35                  40                  45

Gly Asn Ser Gly Lys Met His Glu Tyr Cys Ser Pro Ser Thr Thr Leu
    50                  55                  60

Pro Asp Met Leu Asp Gly Tyr Gln Lys Thr Ser Gly Arg Arg Leu Trp
65                  70                  75                  80

Asp Ala Lys His Glu Asn Leu Ser Asn Glu Ile Asp Arg Ile Lys Lys
                85                  90                  95

Glu Asn Asp Ser Met Gln Val Lys Leu Arg His Leu Lys Gly Glu Asp
            100                 105                 110

Ile Asn Ser Leu Asn His Lys Glu Leu Met Val Leu Glu Glu Gly Leu
        115                 120                 125

Thr Asn Gly Leu Ser Ser Ile Ser Ala Lys Gln Ser Glu Ile Leu Arg
    130                 135                 140
```

```
Ile Val Arg Lys Asn Asp Gln Ile Leu Glu Glu His Lys Gln Leu
145                 150                 155                 160

Gln Tyr Ala Leu His Gln Lys Glu Met Ala Ala Met Gly Gly Asn Met
                165                 170                 175

Arg Met Ile Glu Glu Val Tyr His Gln Arg Asp Arg Asp Tyr Glu Tyr
            180                 185                 190

Gln Gln Met Pro Phe Ala Leu Arg Val Gln Pro Met Gln Pro Asn Leu
        195                 200                 205

His Glu Arg Met
    210

<210> SEQ ID NO 16
<211> LENGTH: 210
<212> TYPE: PRT
<213> ORGANISM: Petunia x hybrida

<400> SEQUENCE: 16

Met Gly Arg Gly Lys Ile Glu Ile Lys Arg Ile Glu Asn Ser Ser Asn
1               5                   10                  15

Arg Gln Val Thr Tyr Ser Lys Arg Arg Asn Gly Ile Leu Lys Lys Ala
            20                  25                  30

Lys Glu Ile Ser Val Leu Cys Asp Ala Arg Val Ser Val Ile Ile Phe
        35                  40                  45

Ala Ser Ser Gly Lys Met His Glu Phe Ser Ser Thr Ser Leu Val Asp
    50                  55                  60

Ile Leu Asp Gln Tyr His Lys Leu Thr Gly Arg Arg Leu Leu Asp Ala
65                  70                  75                  80

Lys His Glu Asn Leu Asp Asn Gln Ile Asn Lys Val Lys Lys Asp Asn
                85                  90                  95

Asp Asn Met Gln Ile Glu Leu Arg His Leu Lys Gly Glu Asp Ile Thr
            100                 105                 110

Ser Leu Asn His Arg Glu Leu Met Ile Leu Glu Asp Ala Leu Glu Asn
        115                 120                 125

Gly Leu Thr Ser Ile Arg Asn Lys Gln Asn Glu Val Leu Arg Met Met
    130                 135                 140

Arg Lys Lys Thr Gln Ser Met Glu Glu Glu Gln Asp Gln Leu Asn Cys
145                 150                 155                 160

Gln Leu Arg Gln Leu Glu Ile Ala Thr Met Asn Arg Asn Met Gly Glu
                165                 170                 175

Ile Gly Glu Val Phe Gln Gln Arg Glu Asn His Asp Tyr Gln Asn His
            180                 185                 190

Met Pro Phe Ala Phe Arg Val Gln Pro Met Gln Pro Asn Leu Gln Glu
        195                 200                 205

Arg Leu
    210
```

US 7,217,859 B2

GENETIC ELEMENTS FROM FBP3 OF *PETUNIA* CONFERRING FLOWER SPECIFIC TRANSGENE EXPRESSION

ACKNOWLEDGEMENT OF FEDERAL RESEARCH SUPPORT

This invention was made, at least in part, with funding from the United States Department of Agriculture. Accordingly, the United States Government may have certain rights in this invention.

BACKGROUND OF THE INVENTION

1. Field of the Invention

The invention relates to recombinant promoters that are capable of driving tissue-specific expression, and transgenes comprising such recombinant promoters. In particular, the invention relates to transgenes comprising a recombinant promoter capable of driving tissue-specific expression of a heterologous nucleic acid molecule in a floral organ. The invention also relates to methods for using such transgenes to produce a protein in a host cell or transgenic plant. The invention further relates to methods for producing a transgenic plant that produces longer-lasting flowers as compared to a wild type plant.

2. Background of the Invention

Ethylene is a plant hormone that plays a critical role in regulating flower senescence in many species. Isolation of several components of the ethylene synthesis and signal transduction pathways has made possible the manipulation of ethylene responses through genetic modification. For example, overexpression of etr1-1, a mutant form of an *Arabidopsis* ethylene receptor caused decreased sensitivity to ethylene in petunia and carnation and delayed flower senescence. See e.g., Wilkinson et al., (1997) A dominant mutant receptor from *Arabidopsis* confers ethylene insensitivity in heterologous plants. Nat. Biotechnol. 15: 444–447; Bovy et al., (1999) Heterologous expression of the *Arabidopsis* etr1-1 allele inhibits the senescence of carnation flowers. Mol. Breed. 5: 301–308).

Although manipulation of ethylene responses is useful to prevent flower senescence, there are several potential disadvantages to this approach. The greatest disadvantage is that where constitutive promoters, such as Cauliflower mosaic virus 35S promoters, were used to drive transgene expression, changes occurred in ethylene response even in untargeted tissues. In fact, etr1-1 has been shown to have negative effects when expressed ectopically in vegetative tissues such as roots and stems. For example, ethylene-insensitive petunia that harbors Cauliflower mosaic virus 35S promoter driven etr1-1 displays reduced adventitious rooting. See e.g., Clark et al., (1999) Root formation in ethylene-insensitive plants. Plant Physiol. 121: 53–60. These plants also show a great deal of premature death. See e.g., Shibuya et al., (2004) The central role of PhEIN2 in ethylene responses throughout plant development in petunia (Unpublished). Furthermore, overexpression of etr1-1 in tobacco increased susceptibility to fungal pathogens infecting roots. See e.g., Knoester et al., (1998) Ethylene-insensitive tobacco lacks non-host resistance against soil-borne fingi. Proc. Natl. Acad. Sci. 95: 1933–1937. Thus, altering ethylene sensitivity throughout the plant causes negative effects in untargeted tissues.

Therefore, there remains a need in the art for recombinant promoters that are capable of driving tissue-specific expression of an isolated nucleic acid molecule operably linked to the promoter. In particular, there is a need in the art for recombinant promoters that are capable of driving expression of isolated nucleic acid molecules in a floral organ, and transgenes comprising such recombinant promoters. The development of such transgenes would have wide application in the production of transgenic plants expressing commercially desirable proteins, such as ethylene receptor etr1-1, in floral organs.

SUMMARY OF THE INVENTION

The present invention provides recombinant promoters that drive tissue-specific expression of an isolated nucleic acid molecule operably linked to the promoter. Specifically, the invention provides a recombinant promoter comprising the nucleotide sequence of any of SEQ ID NO: 9, SEQ ID NO: 10, SEQ ID NO: 11, or SEQ ID NO: 12; or a portion of the nucleotide sequence of any of SEQ ID NO: 9, SEQ ID NO: 10, SEQ ID NO: 11, or SEQ ID NO: 12. In one embodiment, the recombinant promoters of the invention drive expression of the nucleic acid molecule in a floral organ.

The present invention also provides vectors, host cells, and transgenic plants comprising recombinant promoters capable of driving tissue-specific expression of an isolated nucleic acid molecule operably linked to the promoter.

The present invention further provides transgenes comprising recombinant promoters that drive tissue-specific expression and an isolated nucleic acid molecule operably linked to the promoter. Specifically, the invention provides transgenes in which the recombinant promoter comprises the nucleotide sequence of any of SEQ ID NO: 9, SEQ ID NO: 10, SEQ ID NO: 11, or SEQ ID NO: 12; or a portion of the nucleotide sequence of any of SEQ ID NO: 9, SEQ ID NO: 10, SEQ ID NO: 11, or SEQ ID NO: 12. In one embodiment, the transgenes of the invention comprise recombinant promoters that drive expression of the nucleic acid molecule in a floral organ.

The present invention also provides vectors, host cells, and transgenic plants comprising transgenes containing recombinant promoters that drive tissue-specific expression of an isolated nucleic acid molecule operably linked to the promoter.

The present invention further provides methods for using transgenes comprising recombinant promoters that drive tissue-specific expression of an isolated nucleic acid molecule operably linked to the promoter to produce a protein in a host cell or transgenic plant. In one method of the invention, a protein encoded by a transgene comprising a recombinant promoter capable of driving tissue-specific expression of an isolated nucleic acid molecule operably linked to the promoter is produced by introducing the transgene into a host cell and then culturing the host cell under suitable conditions to express the protein. In another method of the invention, a protein encoded by a transgene comprising a recombinant promoter that drives tissue-specific expression of an isolated nucleic acid molecule operably linked to the promoter is produced by introducing the transgene into a plant cell or tissue and then regenerating a transgenic plant from the transformed plant cell or transformed plant tissue.

The invention also provides methods for producing a transgenic plant that produces longer-lasting flowers as compared to a wild type plant. In one method of the invention, a transgene comprising a recombinant promoter that drives tissue-specific expression of an isolated nucleic acid molecule operably linked to the promoter and a heterologous sequence for ethylene receptor etr1-1 is introduced into a plant cell or plant tissue and then regenerating a transgenic plant from the transformed plant cell or transformed plant tissue.

Specific embodiments of the present invention will become evident from the following more detailed description of certain preferred embodiments and the claims.

DETAILED DESCRIPTION OF THE INVENTION

Figure 1:
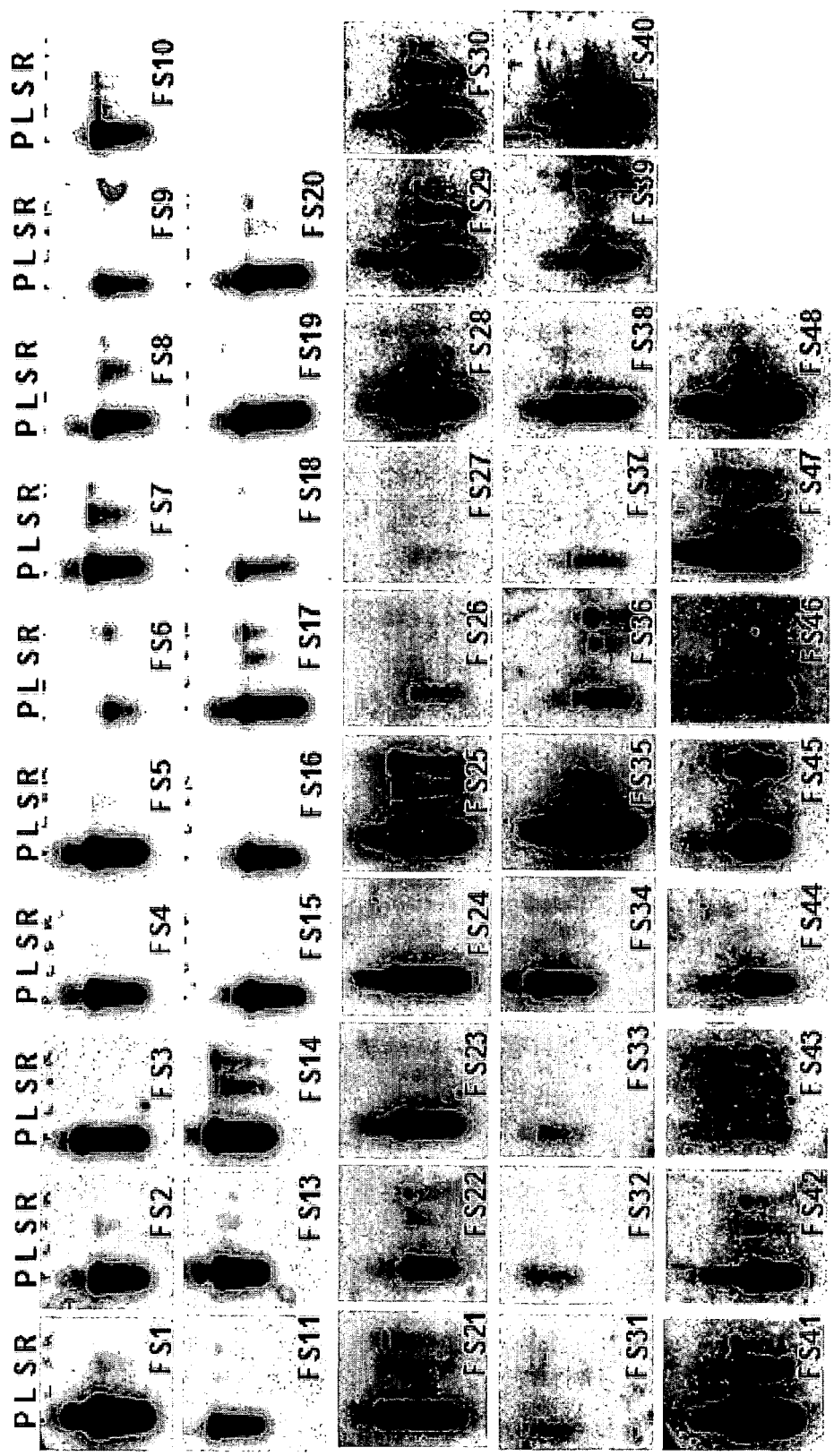
FIG. 1 shows the results of RNA gel blot analysis using probes derived from flower-specific genes identified by cDNA microarray analysis; gene expression was analyzed in RNA isolated from petals at anthesis (first lane), leaves (second lane), stems (third lane), and roots (fourth lane). Twenty μg of total RNA isolated from petals (at anthesis), leaves, stems and roots was separated on a formaldehyde-agarose gel and blotted onto a nylon membrane. The blots were hybridized with 32P-labeled cDNA probes and exposed to autoradiography film for 48 hr at −80 C. P, petal; L, leaf; S, stem; R, root.

The present invention provides recombinant promoters that drive tissue-specific expression, and transgenes comprising such recombinant promoters. In particular, the invention provides transgenes comprising a recombinant promoter that drives tissue-specific expression of a nucleic acid molecule in a floral organ. The invention also provides methods for using such transgenes to produce a protein in a host cell or transgenic plant. The invention further provides methods for producing a transgenic plant that produces longer-lasting flowers as compared to a wild type plant.

The term "recombinant promoter" or "promoter," as used herein, means a nucleic acid molecule usually found upstream, i.e., 5', of a coding sequence that directs transcription of a nucleic acid sequence into mRNA. A promoter typically comprises a recognition site capable of directing RNA polymerase to initiate RNA synthesis at an appropriate transcription initiation site. A promoter can additionally comprise other sequences such as upstream promoter elements that can influence transcription initiation rate.

The activity or strength of a promoter can be measured by the amount of mRNA it produces or by the amount of protein accumulation in a cell or tissue relative to a promoter whose transcriptional activity is known. The activity or strength of a promoter can be expressed relative to a well-characterized promoter. For example, a promoter can be operably linked to a reporter sequence (e.g., GUS) and introduced into a specific cell type. A known promoter can be similarly prepared and introduced into the same cell. Transcriptional activity of the promoter is then determined by comparing the amount of reported expression, relative to the known promoter.

An isolated promoter sequence of the instant invention can be modified to provide for a range of expression levels of the coding sequence. Less than the entire promoter region can be used and the ability to drive tissue-preferred expression retained. Expression levels of mRNA can be decreased with deletions of portions of the promoter sequence. Thus, the promoter can be modified to be a weak or strong promoter. A weak promoter drives expression of a coding sequence at a low level. A strong promoter drives expression of a coding sequence at a high level.

Enhancers can be used in combination with the promoters of the invention. Enhancers are nucleotide sequences that increase expression. Enhancers are known in the art and include, for example, an SV40 enhancer region and a 35S enhancer element.

In one embodiment, recombinant promoters of the invention comprise the nucleotide sequence of any of SEQ ID NO: 9, SEQ ID NO: 10, SEQ ID NO: 11, or SEQ ID NO:12. Recombinant promoters of the invention also include portions of the nucleotide sequence of any of SEQ ID NO: 9, SEQ ID NO: 10, SEQ ID NO: 11, or SEQ ID NO:12 that drive tissue-specific expression of an isolated nucleic acid molecule.

One embodiment of the invention provides a minimal promoter. A minimal promoter will typically comprise a TATA box and transcriptional start sequence, but will not contain additional stimulatory and repressive elements. The boundaries defining the minimal promoter sequence can be ambiguous. That is, the nucleotide positions defining the 5' and 3' ends of a minimal promoter can vary slightly depending on, for example, the expression-reporter system used. The boundaries defining the minimal promoter can be determined using known techniques, described in, for example, Fang et al., (1989) Plant Cell 1:141–50 and Odell et al., (1985) Nature 313:810–2.

The invention also provides promoters wherein promoter sequences are duplicated. The duplication can provide enhanced promoter activity. For example, two or more copies of an enhancer element in tandem often results in increased expression levels. See e.g., U.S. Pat. No. 5,424, 200; Maiti et al., (1997) Transgenic Res. 6:143–56; and Maiti & Shepard (1998) Biochem. Biophys. Res. Commun. 244:440–44.

The invention also provides chimeric promoters comprising a portion of a promoter of the invention. For example, a chimeric promoter can comprise one or more promoter elements of the invention combined with one or more promoter elements derived from another promoter of the invention or any other promoter. The portion of a chimeric promoter that is not derived from a promoter of the invention can be derived from, for example, another plant promoter or a viral promoter, or from any other naturally occurring promoter. Alternatively, that portion can be synthetic or a modified variation or a naturally-occurring promoter.

Fragments or portions of a promoter nucleotide sequence disclosed herein are also encompassed by this invention. Such fragments will comprise at least about 20, 50, 75, 100, 150, 200, 300, 400, 500, 750, 1,000, 1,250, 1,500, 1,750, or 2,000 contiguous nucleotides of the promoter nucleotide sequence disclosed herein. Such fragments will usually comprise the TATA recognition motif of the promoter sequence. A fragment or portion of the invention can comprise one or more TATA signals and/or one or more Transcription Factor Binding sites as shown in Tables 2 and 3 below.

Such fragments can be obtained by use of restriction enzymes to cleave the naturally-occurring promoter nucleotide sequences disclosed herein; by synthesizing a nucleotide sequence; through the use of, e.g., PCR technology. See e.g., Mullis et al. (1987) Methods Enzymol. 155: 335–350, and Erlich, ed. (1989) PCR Technology (Stockton Press, New York). Fragments of promoter sequences are capable of driving tissue-preferred expression and are useful as probes to identify similar sequences.

An example of a promoter fragment or a portion thereof is a promoter formed by one or more deletions from a larger promoter. The 5' portion of a promoter up to the TATA signal near the transcription start site can typically be deleted without abolishing promoter activity, as described by Zhu et al., The Plant Cell 7: 1681–89 (1995). Such fragments retain promoter activity, particularly the ability to drive expression in specific tissues. Promoter activity can be measured by, for example, RNA gel blot analysis and reporter activity measurements when using transcriptional fusions. See, for example, Sambrook et al. (1989) Molecular Cloning: A Laboratory Manual (2nd ed. Cold Spring Harbor Laboratory, Cold Spring Harbor, N.Y.).

The term "isolated nucleic acid molecule" is used to refer to a nucleic acid molecule that (1) has been separated from at least about 50 percent of proteins, lipids, carbohydrates, or other materials with which it is naturally found when total nucleic acid is isolated from source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with, for example, its use in polypeptide production.

The term "nucleic acid sequence" or "nucleic acid molecule" is used to refer to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "identity," as known in the art, is used to refer to a relationship between two or more nucleic acid molecules or polypeptide molecules, as determined by comparing the sequences. In the art, "identity" also means the degree of sequence relatedness between nucleic acid molecules or polypeptide molecules, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "tissue-specific expression," as it relates to promoter activity, refers to the ability of a promoter to drive the expression of an isolated nucleic acid molecule in less than all of the tissues of an organism into which the promoter and nucleic acid molecule are introduced. The term "constitutive expression," as it relates to promoter activity, refers to the ability of a promoter to drive the expression of an isolated nucleic acid molecule in substantially all of the tissues of an organism into which the promoter and nucleic acid molecule are introduced. In one embodiment, the recombinant promoters of the invention drive tissue-specific expression of an isolated nucleic acid molecule. In another embodiment, the recombinant promoters of the invention drive expression of an isolated nucleic acid molecule in a specific tissue. In yet another embodiment, recombinant promoters of the invention drive the expression of an isolated nucleic acid molecule in a floral organ. Promoters of the invention are floral organ specific. That is, the promoters drive expression of a nucleic acid sequence such that the level of the resulting mRNA in the floral organ is expressed at a level that is about 5 fold, 10 fold, 100 fold, 1,000 fold, or more higher than another tissue or organ. The level of mRNA can be measured either at a single time point or at multiple time points and as such the increase in mRNA can be an average increase or an extrapolated value derived from experimentally measured values.

The recombinant promoters and nucleic acid molecules of the invention can readily be obtained in a variety of ways including, without limitation, chemical synthesis, genomic library screening, expression library screening, or PCR amplification of genomic DNA. Recombinant nucleic acid methods used herein are generally those set forth in Sambrook et al., *Molecular Cloning: A Laboratory Manual* (Cold Spring Harbor Laboratory Press, 1989) or *Current Protocols in Molecular Biology* (Ausubel et al., eds., Green Publishers Inc. and Wiley and Sons 1994).

One method for obtaining the recombinant promoters and nucleic acid molecules of the invention is the polymerase chain reaction (PCR). In this method, genomic DNA isolated from plant tissue is used as a template for PCR amplification. Two primers, typically complementary to two separate regions of a particular nucleic acid sequence, are then added to the nucleic acid sequence along with a polymerase such as Taq polymerase, and the polymerase amplifies the region of the nucleic acid sequence between the two primers.

Another method for obtaining the recombinant promoters and nucleic acid molecules of the invention is chemical synthesis using methods well known to the skilled artisan such as those described by Engels et al., 1989, *Angew. Chem. Intl. Ed.* 28:716–34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the desired nucleic acid molecule will be several hundred nucleotides in length. Nucleic acids larger than about 100 nucleotides can be synthesized as several fragments using these methods. The fragments can then be ligated together to form the full-length nucleotide sequence. Other methods known to the skilled artisan can be used as well.

The term "transgene," as used herein, refers to a chimeric gene comprising a recombinant promoter and an isolated nucleic acid molecule operably linked to the promoter, wherein the chimeric gene is capable of integrating into the germ line of an organism and being expressed. In one embodiment, the transgenes of the invention comprise a recombinant promoter operably linked to a nucleic acid molecule encoding ethylene receptor etr1-1. In other embodiments, transgenes of the invention comprise a recombinant promoter operably linked to a nucleic acid molecule encoding, for example polypeptides that play a role in determining flower pigmentation, fragrance, seed yield. Other nucleic acid molecules can encode, for example, proteins having commercial value such as pharmaceuticals.

The term "operably linked" is used to refer to an arrangement of flanking sequences wherein the flanking sequences so described are configured or assembled so as to perform their usual function. Thus, a flanking sequence operably linked to a coding sequence can be capable of effecting the replication, transcription, or translation of the coding sequence. For example, a coding sequence is operably linked to a promoter when the promoter directs transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "vector" is used to refer to any molecule (e.g., nucleic acid, plasmid, or virus) used to transfer coding information to a host cell. Vectors containing the transgenes of the invention can be prepared by inserting a recombinant promoter and an isolated nucleic acid molecule into an appropriate vector using standard ligation techniques. Typically, the vectors of the invention will also contain sequences (in addition to the recombinant promoter and isolated nucleic acid molecule) for plasmid maintenance and for cloning and expression of exogenous nucleotide sequences. Such sequences, or "flanking sequences," typically include one or more of the following: one or more enhancer sequences, an origin of replication, a transcriptional termination sequence, a sequence encoding a leader sequence for polypeptide secretion, a polyadenylation sequence, a polylinker region for inserting the nucleic acid encoding the polypeptide to be expressed, and a selectable marker element. In preferred embodiments, a recombinant promoter and isolated nucleic acid molecule are introduced into a transformation vector such as, pHK, for example, that contains spectromycin resistance gene as a selectable marker for host bacteria and a kanamycin resistance gene as a selectable marker for a host plant.

Flanking sequences can be homologous (i.e., from the same species or strain as the host cell), heterologous (i.e., from a species other than the host cell species or strain), hybrid (i.e., a combination of flanking sequences from more than one source), or synthetic. As such, the source of a flanking sequence may be any prokaryotic or eukaryotic organism, any vertebrate or invertebrate organism, or any plant, provided that the flanking sequence is functional in, and can be activated by, the host cell machinery.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector.

A transcription termination sequence is typically located 3' of the end of a polypeptide coding region and serves to terminate transcription. While a transcription termination sequence is easily cloned from a library or even purchased commercially as part of a vector, it can also be readily synthesized using methods for nucleic acid synthesis such as those described herein. In one embodiment, vectors of the invention contain a nopaline synthase gene terminator sequence (NOS3') for terminating transcription of an isolated nucleic acid molecule operably linked to the recombinant promoter.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin; (b) complement auxotrophic deficiencies of the cell; or (c) supply critical nutrients not available from complex media. Selectable markers include, for example, kanamycin resistance, the ampicillin resistance, and tetracycline resistance. Neomycin resistance can also be used for selection in prokaryotic and eukaryotic host cells.

Vectors of the invention can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

The term "host cell," as used herein, refers to a cell that has been transformed, or that can be transformed with a nucleic acid sequence. The term includes the progeny of the parent cell, whether or not the progeny is identical in morphology or in genetic make-up to the original parent, so long as the selected nucleic acid is present.

The vectors of the invention can be inserted into a suitable host cell for amplification or polypeptide expression. The transformation of vectors of the invention into a selected host cell can be accomplished by well known methods including transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

The term "transfection," as used herein, refers to uptake of foreign or exogenous nucleic acid by a cell, and a cell has been "transfected" when the exogenous nucleic acid has been introduced inside the cell membrane. A number of transfection techniques are well known in the art. Such techniques can be used to introduce one or more exogenous nucleic acid moieties into suitable host cells.

The term "transformation" is used to refer to a change in a cell's genetic characteristics, and a cell has been transformed when it has been modified to contain a new nucleic acid. For example, a cell is transformed where it is genetically modified from its native state. Following transfection, for example, transforming nucleic acid can recombine with that of the cell by physically integrating into a chromosome of the cell, can be maintained transiently as an episomal element without being replicated, or can replicate independently as a plasmid. A cell is considered to have been stably transformed when the nucleic acid is replicated with the division of the cell.

The term "naturally occurring" or "native" when used in connection with biological materials such as nucleic acid molecules, polypeptides, host cells, and the like, refers to materials that are found in nature and are not manipulated by man. Similarly, "non-naturally occurring" or "non-native" as used herein refers to a material that is not found in nature or that has been structurally modified or synthesized by man.

Host cells may be prokaryotic host cells (such as *E. coli*), eukaryotic host cells (such as a yeast, insect, or vertebrate cell), or plant cells. In a preferred embodiment, the host cell is a plant cell. A number of suitable host cells are known in the art and many are available from the American Type Culture Collection (ATCC), Manassas, Va. Examples include, but are not limited to, plants whose flower senescence is accelerated by ethylene, for example, Petunia (*Petunia hybrida*), Carnation (*Dianthus caryophyllus*), Cyclamen (*Cyclamen* spp.), Delphinium (*Delphinium* spp.), Geranium (*Pelargonium* & *Geranium* spp.), Sweet pea (*Lathyrus odoratus*), Snapdragon (*Antirrhinum majus*), Begonia (*Begonia* sp.), Rose (*Rosa* spp.).

Candidate cells can be genotypically deficient in the selectable marker gene, or can contain a dominantly acting selectable marker gene.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like can also be employed in this method.

Host cells comprising transgenes or vectors of the invention can be cultured using standard media well known to the skilled artisan. The media will usually contain all nutrients necessary for the growth and survival of the cells. Typically, an antibiotic or other compound useful for selective growth of transfected or transformed cells is added as a supplement to the media. The compound to be used will be dictated by the selectable marker element present on the vector with which the host cell was transformed. For example, where the selectable marker element is kanamycin resistance, the compound added to the culture medium will be kanamycin. Other compounds for selective growth include ampicillin, tetracycline, and neomycin.

The amount of protein produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, or activity assays such as DNA binding gel shift assays.

In a preferred embodiment, a commercially desirable protein is produced in a transgenic plant by introducing a transgene comprising a recombinant promoter and an isolated nucleic acid molecule encoding the commercially desirable protein, wherein the nucleic acid molecule is operably linked to the promoter, into a plant cell or tissue; regenerating a transgenic plant from the transformed plant cell or transformed plant tissue; and then growing the transgenic plant under suitable conditions to express the protein. In one embodiment, a vector comprising the transgene is introduced into a plant cell or tissue using *Agrobacterium*-mediated transformation. The transformation vectors are transferred to *Agrobacterium* through triparental mating. Plant tissue is transformed with this construct through *Agrobacterium*-mediated transformation. Transformants are selected on tissue culture media containing appropriate antibiotics. In another embodiment, the transgene encodes ethylene receptor etr1-1, and the transgenic plants thus obtained produce longer-lasting flowers as compared to a wild type plant The invention also provides methods for producing transgenic plants or plant cells comprising a promoter of the invention operably linked to a heterologous nucleic acid sequence. Other nucleic acid sequences can also be introduced into the plant or plant cell along with the promoter. These other nucleic acid sequences can include 3' transcriptional terminators, 3' polyadenylation signals, other untranslated nucleic acid sequences, transit or targeting sequences, selectable markers, enhancers, and operators.

A suitable plant cell is selected and transformed with a recombinant vector. The transformed host cell is cultured under conditions effective to produce a plant.

The regeneration, development, and cultivation of plants from transformed plant protoplast or explants is well know in the art. See e.g., Dodds & Roberts, Experiments in Plant Tissue Culture, 1995, Cambridge University Press, New York; Davey (ed.), *Agrobacterium* Protocols, 1995, Humana Press, New Jersey; Smith, Plant Tissue Culture, 2000, Academic Press, New York. For example, transformants are generally cultured in the presence of a selective media that selects for successfully transformed cells and induces the regeneration of plant shoots. The shoots are transferred to an appropriate root-inducing medium containing a selective agent and an antibiotic to prevent bacterial growth. Shoots that develop roots are transplanted to soil or other media to allow the continued development of roots.

The Examples, which follow, are illustrative of specific embodiments of the invention, and various uses thereof. They are set forth for explanatory purposes only, and are not to be taken as limiting the invention.

EXAMPLE 1

Identification of Flower Petal-Specific Genes

Flower petal-specific genes were identified by first preparing individual cDNA libraries from petunia flowers (*Petunia hybrida* cv. Mitchell) isolated either (1) at various stages of floral development, (2) following pollination, or (3) following exogenous ethylene treatment. The first cDNA library (floral development) was prepared from pooled mRNA isolated from whole flowers collected at six developmental stages between floral initiation and anthesis. The second cDNA library (post-pollination) was prepared from pooled mRNA isolated from whole flowers that were pollinated at anthesis and then collected at regular intervals for 48 hours following pollination. The final cDNA library (ethylene-treated) was constructed from pooled mRNA isolated from whole flowers that were treated with 2 μL/L ethylene at anthesis and then collected at regular intervals until 24 hours following the onset of treatment. Each cDNA library was prepared using bacteriophage vectors that allowed for uni-directional cloning of the cDNA inserts (λ ZAP® II; Stratagene; La Jolla, Calif.).

Several random cDNA clones from each library were sequenced to assess the quality of the libraries, and then primary (unamplified) library stocks were excised and introduced into bacterial cells. *E. coli* containing the excised phagemids were plated, and 10% of the colonies on each plate were selected at random for DNA sequencing analysis. DNA sequence data obtained from approximately 6805 clones indicated that between 40–50% of these clones contained redundant sequences, resulting in the identification of approximately 3200 non-redundant cDNAs.

To prepare microarrays containing the non-redundant sequences, bacterial cultures containing each of the non-redundant cDNAs were grown up, and the cDNA sequences were isolated by PCR amplification. Microarrays were generated using an AFFYMETRIX™ 418™ arrayer (Santa Clara, Calif.) by spotting the PCR-amplified cDNAs in duplicate onto glass microscope slides coated with poly-L-lysine solution. The slides were then UV crosslinked and denatured prior to DNA hybridization analysis.

Flower-specific genes were identified on the microarrays by hybridization with probes generated from (a) total RNA extracted from *P. hybrida* cv Mitchell's petals and (b) pooled total RNA extracted from vegetative tissues (i.e., leaf, stem, and root). Fluorescent probes were prepared by reverse transcribing mRNA from total RNA using dye-specific primers (cy3 or cy5; SUBMICRO™ EX Expression Array Detection Kit; Genisphere; Hatfield, Pa.), and then were hybridized to the microarray slides for 24 hours. Following hybridization, the slides were washed to remove unbound probe, and then scanned immediately using an AFFYMETRIX™ scanning microscope. Scanned images were analyzed for intensity readings using AFFYMETRIX™ Jaguar 1.0 software. The intensity ratios for the cy3 and cy5 dyes at each spot were used to identify flower-specific genes. Each hybridization experiment was conducted in triplicate by analyzing duplicate spots on three individual slides. Only genes that yielded a flower-specific signal at four or more of the six spots tested were considered for further analysis. Based on microarray analysis, 47 genes were identified as being flower-specific.

Figure 2:
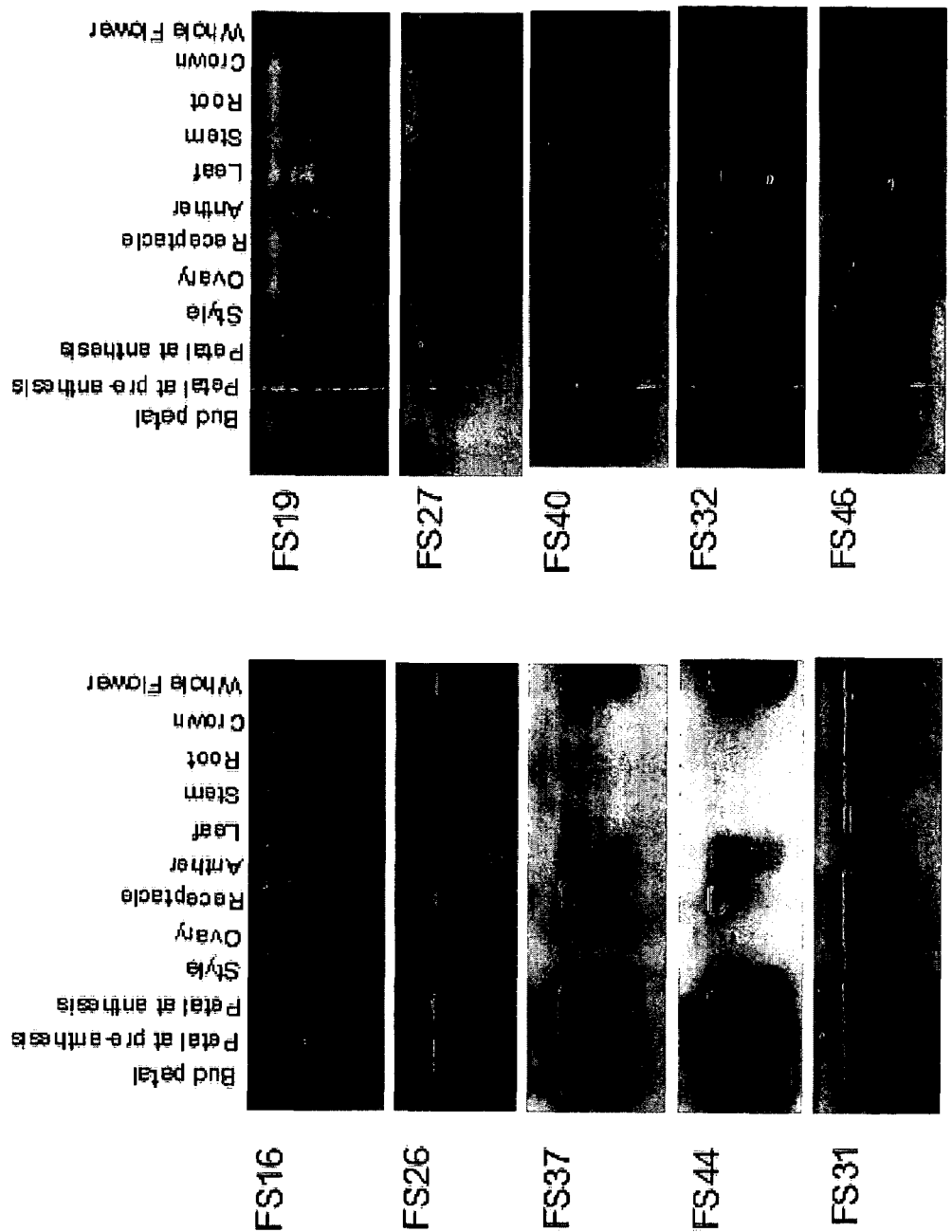
FIG. 2 shows the results of RNA gel blot analysis of flower-specific genes identified in the first screen shown in FIG. 1. Total RNA was isolated from petal at three developmental stages (bud, pre-anthesis and anthesis), style, ovary, receptacle anther, leaf, stem root, and crown). Thirty μg of total RNA was separated on a gel and blotted onto a nylon membrane. The blots were hybridized with 32P-labeled cDNA probes and exposed to films for 7 days at −80 C.
Figure 3:
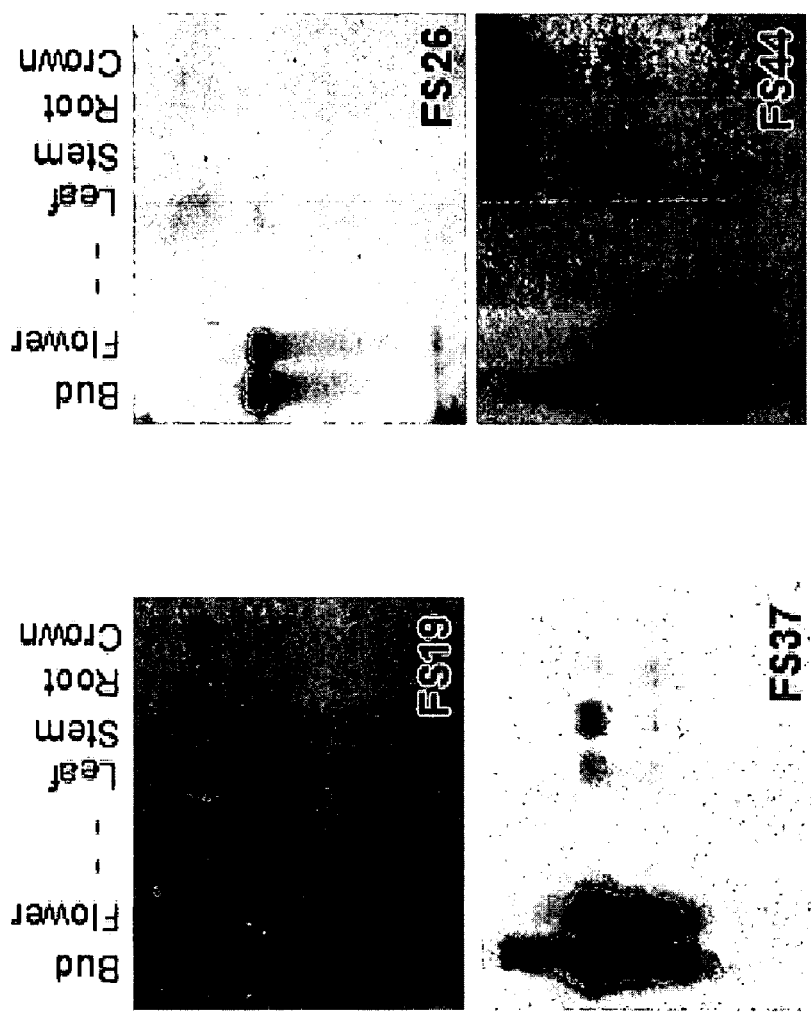
FIG. 3 shows the results of RNA gel blot analysis of flower-specific genes identified in the second screen shown in FIG. 2. Poly(A) RNA was isolated from bud, flower at anthesis, leaf, stem, root and crown. Two μg of poly(A) RNA was separated on a gel and blotted onto a nylon membrane. The blots were hybridized with 32P-labeled cDNA probes and exposed to films for 7 days at −80 C.

RNA gel blot analysis was performed to confirm the flower-specific expression of genes identified by microarray analysis. RNA gel blots were prepared by first separating 20 μg of total RNA from petal, leaf, stem, and root tissue on a formaldehyde-agarose gel, and then blotting the gels onto a nylon membrane. Blots were hybridized with $^{32}$P-labeled cDNA probes generated from the flower-specific genes to be tested, and then the blots were washed and exposed to film for 48 hours (FIG. 1). Based on the results of a first screen of the flower-specific genes identified by microarray analysis, sixteen genes were confirmed as being flower-specific, and their full-length cDNA inserts were re-sequenced. Sequence alignment analysis revealed that ten of the sixteen genes were unique. Subsequently, second and third screens were performed using either 30 μg of total RNA (second screen; FIG. 2) or 2 μg of Poly-(A) RNA (third screen; FIG. 3) extracted from several tissues and developmental stages.

Four flower-specific genes, designated as FS19, FS26, FS37, and FS44, were selected for promoter isolation. See Table 1. BLAST analysis revealed that flower-specific genes FS37 and FS44 encode proteins that are identical to the floral binding proteins FBP3 and FBP1, respectively (Angenent et al., 1992, *Plant Cell* 4:983–93; Angenent et al., 1994, *Plant J.* 5:33–44). The flower-specific gene FS19 was found to encode a protein sharing 56% identity with a putative amp-binding protein in *Arabidopsis thaliana* that contains a conserved amp-binding domain. The flower-specific gene FS26 was found to encode a protein sharing 33% identity with an unknown protein in *Arabidopsis thaliana*, and a search of the conserved domain database showed that this protein contained a RING-finger (Really Interesting New Gene) domain.

TABLE 1

| Flower-Specific Gene | Clone # | SEQ ID NO: Of Promoter Sequence | Sequences Identified in BLAST Analysis GenBank Acc. No. Sequence Description; Organism | E-value | Conserved Domain |
| --- | --- | --- | --- | --- | --- |
| FS19 | Petunia-PP11-F02 | 9 | NP_176763 putative amp-binding protein; *Arabidopsis* (SEQ ID NO: 1) (SEQ ID NO: 13) | 0 | AMP-binding |
| FS26 | Petunia-PP7-A09 | 10 | BAC43193 unknown protein; *Arabidopsis* (SEQ ID NO: 2) (SEQ ID NO: 14) | 8e−28 | RING |
| FS37 | Petunia-C2H4-3-F08 | 11 | CAA50549 FBP3; Petunia × hybrida (SEQ ID NO: 3) (SEQ ID NO: 15) | 0 | MADS box |
| FS44 | Petunia-DevA-10-D07 | 12 | Q03488 floral homeotic protein FBP1; Petunia × hybrida (SEQ ID NO: 4) (SEQ ID NO: 16) | 0 | MADS box |

EXAMPLE 2

Identification of Promoter Elements Conferring Flower Petal-Specific Gene Expression A *petunia* genomic library was constructed in order to isolate the promoters of the flower-specific genes identified in Example 1. Genomic DNA was isolated from the flower buds of *P. hybrida* cv. Mitchell, partially digested with Sau3AI, and then ligated into the ZAP EXPRESS® vector (Stratagene). The primary genomic library (1×10$^6$ pfu) was plated on NZY agar plates, and plaques were transferred onto nitrocellulose membranes. The membranes were then hybridized with $^{32}$P-labeled cDNA for FS19, FS26, FS37, and FS44, washed, and exposed to film. Following a secondary screen, insert-containing phagemids were obtained from the isolates by in vivo excision. A 4.4 kb genomic DNA fragment for the flower-specific gene FS37 was isolated and sequenced. For the other three genes (FS19, FS26, and FS44), only short genomic fragments were isolated. In order to obtain longer sequences of the promoter regions for these three genes, genome walking was performed with the UNI- VERSAL GENOMEWALKER™ Kit (BD Biosciences; Palo Alto, Calif.) according to the manufacture's protocols. Upstream DNA sequences of 3.6 kb, 1.8 kb and 2.3 kb, starting from the ATG translation initiation site for FS19, FS26, and FS44, respectively, were obtained by multiple genome walking. A 1074 bp region upstream of the FS44 translation start site was found to be identical to a sequence previously reported as the FBP1 promoter (Angenent et al., 1992).

EXAMPLE 3

Figure 4:
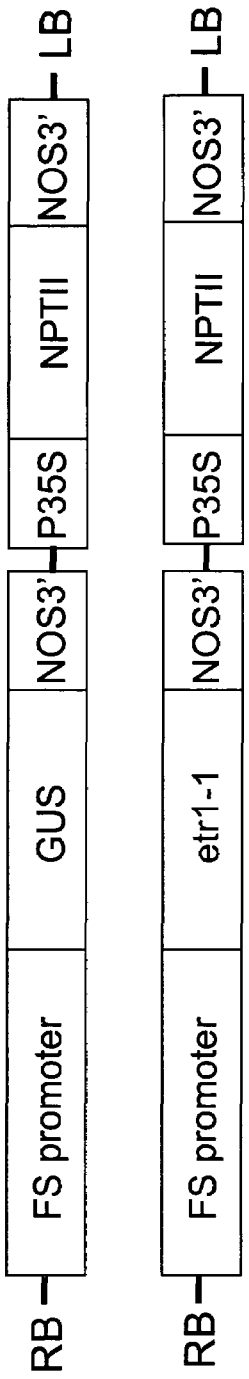
FIG. 4 shows a schematic of two types of transgene constructs that were prepared using flower-specific (FS) promoters and either a β-glucuronidase reporter gene (GUS) or a mutated *Arabidopsis* ethylene receptor etr1-1 sequence (etr1-1).

Preparation of Constructs Containing Flower Petal-Specific Promoter Elements The upstream regions of the flower-specific genes, which contain the ATG translation initiation sites, were amplified by PCR using genomic DNA as a template. PCR products of 2932 bp, 1545 bp, 3040 bp, and 2269 bp corresponding to the promoters for the flower-specific genes FS19, FS26, FS37, and FS44, respectively, were fused to either a GUS (β-glucuronidase) reporter gene (Jefferson et al., 1987, *EMBO J.* 20:3901–07) or a mutated *Arabidopsis* ethylene receptor etr1-1 sequence (Chang et al., 1993, *Science* 262: 539–44), and then were followed by a NOS3' sequence (nopaline synthase gene terminator sequence). It has been reported that the etr1-1 gene confers ethylene insensitivity in heterologous plants including petunia, and results in the extension of flower-life (Wilkinson et al., 1997, *Nat. Biotechnol.* 15:444–47). To generate transgene constructs (FIG. 4), the resulting chimeric genes were inserted into the plant transformation vector pHK, which contains the selectable marker gene NPT II (neomycin phosphotransferase II).

Figure 5:
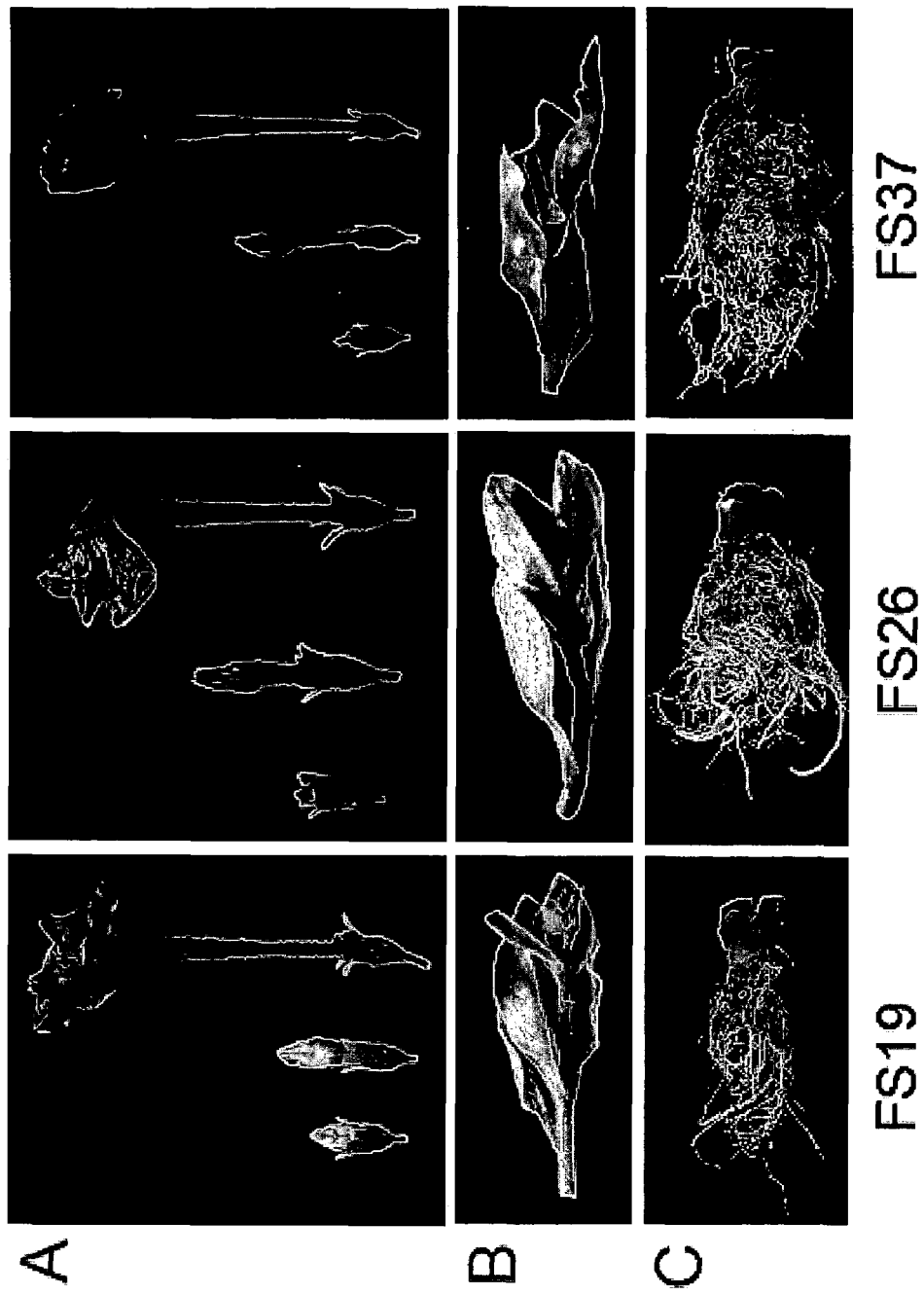
FIG. 5 shows the expression of GUS in the flowers (A), leaves (B), and roots (C) of plants transformed with a transgene construct containing the FS19, FS26 and FS37 promoters.

Leaf explants from *P. hybrida* cv. Mitchell sterile stock plants were transformed with the transgene constructs as described in Jorgensen et al., 1996, *Plant Mol. Biol.* 31:957–73. Transformants were selected on MS media containing 150 µg/mL kanamycin and rooted on MS media containing 200 µg/mL kanamycin. Thirty rooted plants were transferred in soil and grown in normal green house conditions. GUS expression analysis was performed as described in Jefferson et al., 1987, *Plant Mol. Biol. Reporter* 5:387–405. FIGS. 5A–5B show the expression of GUS in the flowers and leaves of plants transformed with a transgene construct containing the FS37 promoter.

EXAMPLE 4

Identification of TATA Signals and Transcription Factor Binding Sites

The promoters were analyzed for putative TATA signals using the WWW Signal Scan (Prestridge, D.S. (1991) SIGNAL SCAN: A computer program that scans DNA sequences for eukaryotic transcriptional elements. CABIOS 7: 203–206) and the PLACE Web Signal Scan (Higo et al. (1999) Plant cis-acting regulatory DNA elements (PLACE) database. Nucleic Acids Research 27: 297–300; Prestridge, (1991) SIGNAL SCAN: A computer program that scans DNA sequences for eukaryotic transcriptional elements. CABIOS 7: 203–206). The results are shown in Table 2.

TABLE 2

| Promoter | Program | Site |
|---|---|---|
| FS19 | WWW Signal Scan | site 2664 (+) TATATAAA |
| FS19 | PLACE Web Signal Scan | site 873 (+) TATAAAT |
| FS19 | PLACE Web Signal Scan | site 2256 (+) TATAAAT |
| FS19 | PLACE Web Signal Scan | site 2300 (+) TATAAAT |
| FS19 | PLACE Web Signal Scan | site 2666 (+) TATAAAT |
| FS19 | PLACE Web Signal Scan | site 380 (+) TATATAA |
| FS19 | PLACE Web Signal Scan | site 406 (+) TATATAA |
| FS19 | PLACE Web Signal Scan | site 2664 (+) TATATAA |
| FS19 | PLACE Web Signal Scan | site 1315 (+) TTATTT |
| FS19 | PLACE Web Signal Scan | site 1659 (+) TTATTT |
| FS19 | PLACE Web Signal Scan | site 1663 (+) TTATTT |
| FS19 | PLACE Web Signal Scan | site 1798 (+) TTATTT |
| FS19 | PLACE Web Signal Scan | site 1838 (+) TTATTT |
| FS26 | PLACE Web Signal Scan | site 1839 (+) TATAAAT |
| FS37 | WWW Signal Scan | site 1232 (+) TATATAAA |
| FS37 | WWW Signal Scan | site 414 (+) TATATAAA |
| FS37 | PLACE Web Signal Scan | site 2256 (+) TATAAAT |
| FS37 | PLACE Web Signal Scan | site 2330 (+) TATAAAT |
| FS37 | PLACE Web Signal Scan | site 414 (+) TATATAA |
| FS37 | PLACE Web Signal Scan | site 1232 (+) TATATAA |
| FS37 | PLACE Web Signal Scan | site 378 (+) TTATTT |
| FS37 | PLACE Web Signal Scan | site 382 (+) TTATTT |
| FS37 | PLACE Web Signal Scan | site 388 (+) TTATTT |
| FS37 | PLACE Web Signal Scan | site 1369 (+) TTATTT |
| FS37 | PLACE Web Signal Scan | site 1518 (+) TTATTT |
| FS44 | WWW Signal Scan | site 1169 (+) TATATAAA |
| FS44 | WWW Signal Scan | site 1741 (+) TATATAAA |
| FS44 | PLACE Web Signal Scan | site 1169 (+) TATATAA |
| FS44 | PLACE Web Signal Scan | site 1741 (+) TATATAA |
| FS44 | PLACE Web Signal Scan | site 1757 (+) TATATAA |
| FS44 | PLACE Web Signal Scan | site 1365 (+) TTATTT |
| FS44 | PLACE Web Signal Scan | site 1569 (+) TTATTT |

The promoters were analyzed for putative transcription factor binding sites using TFSEARCH (See Heinemeyer et al. (1998) Databases on Transcriptional Regulation: RANSFAC, TRRD, and COMPEL. Nucleic Acids Res. 26, 364–370). The results are shown in Table 3.

TABLE 3

| | Transcription Factor Binding Site | | |
|---|---|---|---|
| Promoter | Transcription Factor Binding Site | Gene | Reference |
| FS19 | CTATGGTTAAATAT (96–109) (SEQ ID NO:5) | SBF-1; Species: french bean, *Phaseolus vulgaris* | Lawton et al. (1991) Plant Mol. Biol. 16: 235–249. |
| FS19 | ACTAACCTG (700–708) | maize activator P of flavonoid biosynthetic genes | Grotewold et al. (1994) Cell 76: 543–553. |

TABLE 3-continued

Transcription Factor Binding Site

| Promoter | Transcription Factor Binding Site | Gene | Reference |
|---|---|---|---|
| FS37 | TTAAAATTATTGTA (1566–1579) (SEQ ID NO:6) | Athb-1; Species: mouse-ear cress, *Arabidopsis thaliana* | Sessa et al. (1993) EMBO J. 12: 3507–3517. |
| FS44 | TCCTACCAA (1094–1102) | maize activator P of flavonoid biosynthetic genes | Grotewold et al. (1994) Cell 76: 543–553. |
| FS44 | TAATAGTTAATAAT (1768–1781) (SEQ ID NO:7) | SBF-1; Species: french bean, *Phaseolus vulgaris* | Lawton et al. (1991) Plant Mol. Biol. 16: 235–249. |
| FS44 | ATGAAATTATTGTG (1796–1809) (SEQ ID NO:8) | Athb-1; Species: mouse-ear cress, *Arabidopsis thaliana* | Sessa et al. (1993) EMBO J. 12: 3507–3517. |

It should be understood that the foregoing disclosure emphasizes certain specific embodiments of the invention and that all modifications or alternatives equivalent thereto are within the spirit and scope of the invention as set forth in the appended claims. All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, without changing their ordinary meanings as stated in the MPEP. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

We claim:

1. A recombinant promoter comprising:
   (a) the nucleotide sequence of SEQ ID NO: 11, or
   (b) a portion of the nucleotide sequence of SEQ ID NO: 11, wherein the portion comprises at least about 500 contiguous nucleotides of SEQ ID NO: 11, and wherein the promoter drives floral-specific expression of an isolated nucleic acid molecule operably linked to the promoter.

2. The recombinant promoter of claim 1, wherein the promoter drives expression of the nucleic acid molecule in a floral organ.

3. A vector comprising the recombinant promoter of claim 1.

4. A transgenic plant comprising the vector of claim 3.

5. A host cell comprising the vector of claim 3, wherein the host cell is a plant or bacterial cell.

6. The host cell of claim 5, wherein the host cell is a plant cell.

7. A transgenic plant comprising the host cell of claim 6.

8. A transgene comprising the promoter of claim 1 and an isolated nucleic acid molecule operably linked to the promoter.

9. The transgene of claim 8, wherein the promoter drives expression of the nucleic acid molecule in a floral organ.

10. The transgene of claim 8, wherein the nucleic acid molecule encodes ethylene receptor etr-1-1.

11. A vector comprising the transgene of claim 8.

12. The vector of claim 11, wherein the nucleic acid molecule encodes ethylene receptor etr-1-1.

13. A transgenic plant comprising the vector of claim 11.

14. A host cell comprising the vector of claim 11, wherein the host cell is a plant or bacterial cell.

15. The host cell of claim 14, wherein the host cell is a plant cell.

16. A transgenic plant comprising the host cell of claim 15.

17. A method for producing a protein encoded by the transgene of claim 8 in a plant host cell comprising:
    (a) introducing the transgene of claim 8 into the plant host cell; and
    (b) culturing the plant host cell under suitable conditions to express the protein.

18. The method of claim 17, wherein the transgene encodes ethylene receptor etr-1-1.

19. A method for producing a protein encoded by the transgene of claim 8 in a transgenic plant comprising:
    (a) introducing the transgene of claim 8 into a plant cell or plant tissue;
    (b) regenerating a transgenic plant from the transformed plant cell or transformed plant tissue of (a);
    (c) growing the transgenic plant under suitable conditions to express the protein.

20. The method of claim 19, wherein the transgene encodes ethylene receptor etr-1-1.

21. A method for producing a transgenic plant that produces longer-lasting flowers as compared to a wild type plant comprising:
    (a) introducing the transgene of claim 10 into a plant cell or plant tissue;
    (b) regenerating a transgenic plant from the transformed plant cell or transformed plant tissue of (a); and
    (c) selecting a transgenic plant that produces longer-lasting flowers as compared to a wild type plant.

22. A method for producing a transgenic plant that produces longer-lasting flowers as compared to a wild type plant comprising:
    (a) introducing the vector of claim 12 into a plant cell or plant tissue; and
    (b) regenerating a transgenic plant from the transformed plant cell or transformed plant tissue of (a); and
    (c) selecting a transgenic plant that produces longer-lasting flowers as compared to a wild type plant.

23. A transgenic plant produced by the method of claim 21.

24. A transgenic plant produced by the method of claim 22.

* * * * *